(12) United States Patent
Maurer et al.

(10) Patent No.: US 6,368,831 B1
(45) Date of Patent: *Apr. 9, 2002

(54) TREATMENT OF HYPERPROLIFERATIVE DISORDERS

(75) Inventors: Barry J. Maurer, Sunland; C. Patrick Reynolds, Sherman Oaks, both of CA (US)

(73) Assignee: Childrens Hospital Los Angeles, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/471,944

(22) Filed: Dec. 23, 1999

Related U.S. Application Data

(63) Continuation-in-part of application No. 09/342,019, filed on Jun. 28, 1999
(60) Provisional application No. 60/091,138, filed on Jun. 29, 1998.

(51) Int. Cl.$^7$ ................................................ C12N 15/09
(52) U.S. Cl. ..................... 435/69.2; 435/69.2; 435/15; 435/7.21; 435/7.1; 435/7.23; 435/4; 435/193; 435/110; 514/2; 514/28; 514/25; 514/54; 514/237.8; 514/613; 514/617; 514/1; 536/5; 536/24.5
(58) Field of Search .............................. 514/237.8, 613, 514/1, 617, 25, 54, 28, 2; 435/15, 7.21, 7.1, 7.23, 193, 4, 110, 69.2; 536/5, 24.5

(56) References Cited

U.S. PATENT DOCUMENTS

| | | | |
|---|---|---|---|
| 4,190,594 A | 2/1980 | Gander et al. | 260/404 |
| 4,323,581 A | 4/1982 | Gander | 424/324 |
| 4,665,098 A | 5/1987 | Gibbs et al. | 514/613 |
| 4,816,450 A | 3/1989 | Bell et al. | 514/25 |
| 5,041,441 A | 8/1991 | Radin et al. | 514/237.8 |
| 5,302,609 A | 4/1994 | Shayman et al. | 514/380 |
| 5,464,870 A | 11/1995 | Veronesi et al. | 514/617 |
| 5,599,953 A | 2/1997 | Curley, Jr. et al. | 549/417 |
| 5,635,536 A | 6/1997 | Lyons | 514/558 |
| 5,663,377 A | 9/1997 | Curley, Jr. et al. | 549/417 |
| 5,677,341 A | 10/1997 | Lyons | 514/558 |
| 5,707,649 A | 1/1998 | Inokuchi et al. | 424/450 |
| 5,821,072 A | 10/1998 | Schwartz et al. | 435/15 |

FOREIGN PATENT DOCUMENTS

| | | |
|---|---|---|
| JP | 9-176083 | 7/1997 |
| WO | WO 97/40358 | 10/1997 |

OTHER PUBLICATIONS

Yamada et al., Cellular Molecular Life Science (CMLS), vol. 53, pp. 435–441, 1997.*
Lavie et al., The Journal of Biological Chemistry, vol. 272, No. 3, pp. 1682–1687, 1997.*
Kei–ichi et al., Journal of Biochemistry, vol. 110, pp. 96–102, 1991.*
Khan et al., Biochemical and Biophysical Research Communications, vol. 172, No. 2, pp. 683–691, 1990.*
International Search Report dated Mar. 22, 2001, International Application No. PCT/US00/29996.
Lee et al.; Improved Inhibitors of Glucosylceramide Synthase, *The Journal of Biological Chemistry*, 274(21):14662–14669 (1999).
Abe et al.; Structural and Stereochemical Studies of Potent Inhibitors of Glucosylceramide Synthase and Tumor Cell Growth, *Journal of Lipid Research*, 36(3):611–621 (1995).
Abe et al.; A Novel Enzyme That Catalyzes the Esterification of N–Acetylsphingosine, *The Journal of Biological Chemistry*, 271(24):14383–14389 (1996).
International Search Report PCT/US99/14591; dated Oct. 22, 1999.

* cited by examiner

*Primary Examiner*—Christopher S. F. Low
*Assistant Examiner*—Hope A. Robinson
(74) *Attorney, Agent, or Firm*—Myers Bigel Sibley & Sajovec

(57) ABSTRACT

A method of treating a hyperproliferative disorder in a subject in need of such treatment, comprising administering to said subject, in combination, a treatment effective amount of: (a) a ceramide-generating retinoid such as fenretinide or a pharmaceutically acceptable salt thereof; and (b) at least one (and in certain embodiments at least two) ceramide degradation inhibitor, such as compounds selected from the group consisting of (i) glucosylceramide synthesis inhibitors and/or 1-acylceramide synthesis inhibitors, (ii) sphingosine-1-phosphate synthesis inhibitors, and (iii) protein kinase C inhibitors. A preferred glucosyl ceramide synthesis inhibitor is 1-phenyl-2-palmitoylamino-3-morpholino-1-propanol. A preferred sphingosine-1-phosphate synthesis inhibitor is D-erythro-N,N-dimethylsphingosine. A preferred protein kinase C inhibitor is L-threo-dihydrosphingosine.

30 Claims, 16 Drawing Sheets

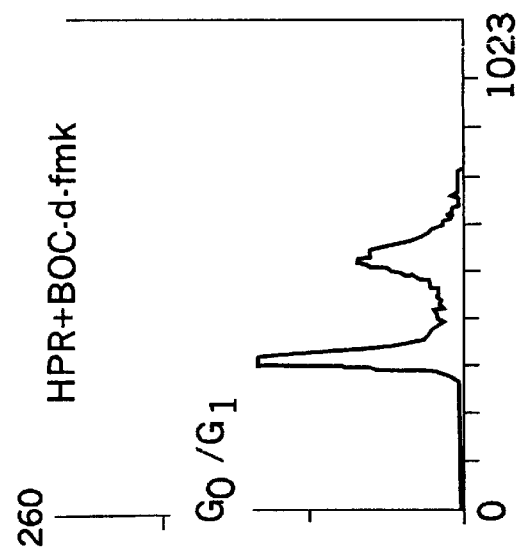
FIG. 18A  FIG. 18B  FIG. 18C
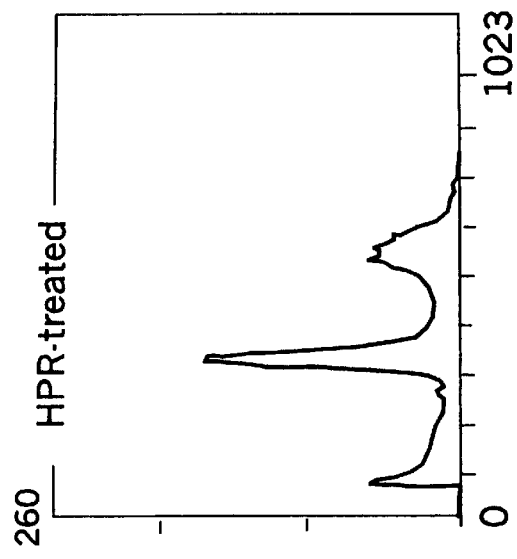
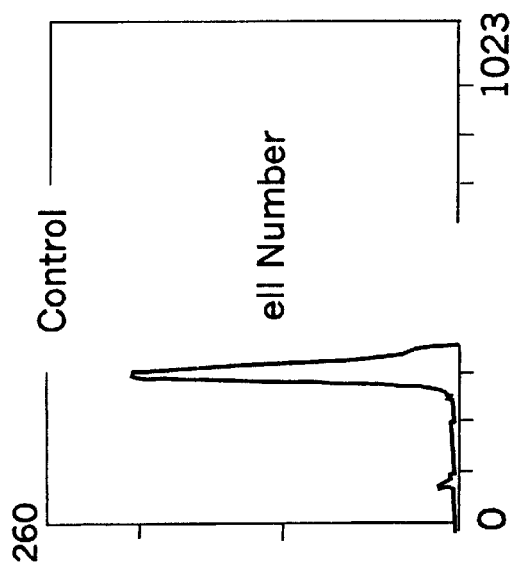

US 6,368,831 B1

TREATMENT OF HYPERPROLIFERATIVE DISORDERS

RELATED APPLICATIONS

This application is a continuation-in-part of copending U.S. patent application Ser. No. 09/342,019, filed Jun. 28,,1999, which in turn claims priority from United States Provisional Application Ser. No. 60/091,138, filed Jun. 29, 1998, the disclosures of both of which are incorporated by reference herein in their entirety.

FIELD OF THE INVENTION

The present invention concerns combination chemotherapy regimes for the treatment of hyperproliferative disorders, and formulations useful for carrying out the same.

BACKGROUND OF THE INVENTION

Fenretinide [HPR; all-trans-N-(4-hydroxyphenyl) retinamide; CAS Registry number 65646-68-6] is currently believed to effect cytotoxicity in cancer cells by generating reactive oxygen species. See, e.g., D. Delia et al., *Carcinogenesis* 18, 943–948 (1997); N. Oridate et al., *J. Natl. Cancer Inst.* 89, 1191–1198 (1997).

U.S. Pat. No. 4,665,098 to Gibbs describes pharmaceutical compositions of fenretinide as useful for the treatment of breast and bladder cancer.

U.S. Pat. No. 5,821,072 to Schwartz et al. provides methods for screening protein kinase C inhibitors capable of potentiating apoptosis in tumor cells, along with methods for screening antitumor therapeutic agents suitable for combination therapy with a protein kinase C inhibitor capable of potentiating apoptosis in tumor cells.

SUMMARY OF THE INVENTION

The present invention is based on the unexpected discovery that fenretinide at appropriate doses generates increased and sustained ceramide in human cancer cell lines. Thus, the cytostatic or cytotoxic activity against hyperproliferative disorders (including neoplastic and nonneoplastic hyperproliferative disorders as defined below) of fenretinide and other such retinoic acid derivatives that generate ceramide can be enhanced by administering an agent that manipulates cellular metabolism and cellular control of ceramide-generated cytotoxicity (e.g., a ceramide degradation inhibitor). Such agents include, but are not limited to, glucosyl ceramide synthase inhibitors, 1-acylceramide synthase inhibitors (or "1-O-acylceramide synthase inhibitors"), sphingosine-1-phosphate synthesis inhibitors, and protein kinase C inhibitors, which may be administered alone or in combination with one another. Specific examples are given below. Preferably, the retinoic acid derivative is given in an amount effective to produce necrosis, apoptosis, or both in the tumor cell, and the ceramide degradation inhibitor is given in an amount effective to increase the necrosis, apoptosis or both produced in the tumor cell over that which would be produced by the retinoic acid derivative alone, or that expected to be produced by the sum of that produced by the retinoic acid derivative and the ceramide degradation inhibitor when given separately (this includes the situation where the combination of both compounds produce an efficacous activity at amounts of the compounds that produce no activity when administered separately).

A method of treating a hyperproliferative disorder in a subject in need of such treatment comprises administering to the subject, in combination, a treatment effective amount of: (a) a retinoic acid derivative that generates ceramide such as fenretinide or a pharmaceutically acceptable salt thereof; and (b) a glucosylceramide synthesis inhibitor (and/or a 1-acylceramide synthesis inhibitor) (including the pharmaceutically acceptable salts thereof) such as 1-phenyl-2-palmitoylamino-3-morpholino-1-propanol or a pharmaceutically acceptable salt thereof. The glucosylceramide synthesis inhibitor (and/or a 1-acylceramide synthesis inhibitor) is administered in an amount effective to enhance the activity of the retinoic acid derivative, such that the two compounds together have an efficacious activity. Preferably, the retinoic acid derivative is given in an amount effective to produce necrosis, apoptosis, or both in the tumor cell, and the glucosylceramide synthesis inhibitor (and/or a 1-acylceramide synthesis inhibitor)is given in an amount effective to increase the necrosis, apoptosis or both produced in the tumor cell over that which would be produced by the retinoic acid derivative alone, or that expected to be produced by the sum of that produced by the retinoic acid derivative and the glucosylceramide synthesis inhibitor (and/or a 1-acylceramide synthesis inhibitor) when given separately. Other compounds including the compounds described herein may also be administered.

Also disclosed is a method of treating a hyperproliferative disorder in a subject in need of such treatment which comprises administering to the subject, in combination, a treatment effective amount of: (a) a retinoic acid derivative that generates ceramide such as fenretinide or a pharmaceutically acceptable salt thereof; and (b) a sphingosine-1-phosphate synthesis inhibitor such as D-erythro-N,N-dimethylsphingosine or a pharmaceutically acceptable salt thereof. The sphingosine-1-phosphate synthesis inhibitor is administered in an amount effective to enhance the activity of the retinoic acid derivative, such that the two compounds together have an efficacious activity. Preferably, the retinoic acid derivative is given in an amount effective to produce necrosis, apoptosis, or both in the tumor cell, and the sphingosine-1-phosphate synthesis inhibitor is given in an amount effective to increase the necrosis, apoptosis, or both produced in the tumor cell over that which would be produced by the retinoic acid derivative alone, or that expected to be produced by the sum of that produced by the retinoic acid derivative and sphingosine-1-phosphate synthesis inhibitor when given separately.

Also disclosed is a method of treating a hyperproliferative disorder in a subject in need of such treatment, the method comprising administering to the subject, in combination, a treatment effective amount of: (a) a retinoic acid derivative that generates ceramide such as fenretinide or a pharmaceutically acceptable salt thereof; and (b) a protein kinase C inhibitor such as L-threo-dihydrosphingosine or a pharmaceutically acceptable salt thereof. The protein kinase C inhibitor is administered in an amount effective to enhance the activity of the retinoic acid derivative, such that the two compounds together have an efficacious activity. Preferably, the retinoic acid derivative is given in an amount effective to produce necrosis, apoptosis or both, in the tumor cell, and the protein kinase C inhibitor is given in an amount effective to increase the necrosis, apoptosis or both produced in the tumor cell over that which would be produced by the retinoic acid derivative alone, or that expected to be produced by the sum of that produced by the retinoic acid derivative and protein kinase C inhibitor when given separately.

Also disclosed is a method of treating a hyperproliferative disorder in a subject in need of such treatment, comprising administering to said subject, in combination, a treatment effective amount of: (a) a ceramide-generating retinoid or a pharmaceutically acceptable salt thereof; and (b) at least two (e.g., 2 or 3) compounds selected from the group consisting of (i) glucosylceramide synthesis inhibitors (and/or 1-acylceramide synthesis inhibitors), (ii) sphingosine-1-phosphate synthesis inhibitors, and (iii) protein kinase C inhibitors. The at least two compounds are administered in an amount effective to enhance the activity of the retinoid, such that the compounds together have an efficacious activity. The at least two compounds may be from the same or a different category. In one embodiment, the at least two compounds comprise a glucosylceramide synthesis inhibitor (and/or a 1-acylceramide synthesis inhibitor) and a sphingosine-1-phosphate synthesis inhibitor. In another embodiment, the at least two compounds comprise a glucosylceramide synthesis inhibitor (and/or a 1-acylceramide synthesis inhibitor) and a protein kinase C inhibitor. In another embodiment, the at least two compounds comprise a sphingosine-1-phosphate synthesis inhibitor and a protein kinase C inhibitor. In another embodiment, the at least two compounds comprise a glucosylceramide synthesis inhibitor (and/or a 1-acylceramide synthesis inhibitor), a sphingosine-1-phosphate synthesis inhibitor, and a protein kinase C inhibitor. Preferably, the retinoic acid derivative is given in an amount effective to produce necrosis, apoptosis or both in the tumor cell, and the at least two other compounds are given in an amount effective to increase the necrosis, apoptosis or both produced in the tumor cell over that which would be produced by the retinoic acid derivative alone, or that expected to be produced by the sum of the that produced by the retinoic acid derivative and the at least two other compounds when given separately.

Formulations comprising the aforesaid combinations of compounds in a single pharmaceutical carrier or vehicle, for carrying out the foregoing treatments, are also an aspect of the instant invention.

The uses of the foregoing compounds for the preparation of a medicament for carrying out the aforesaid treatments are also an aspect of the instant invention.

The foregoing and other objects and aspects of the present invention are explained in detail in the drawings herein and the specification set forth below.

BRIEF DESCRIPTION OF THE DRAWINGS

FIG. 18 shows that at 24 hours, BOC-d-fmk abrogated the sub $G_0/G_1$ DNA-fragmentation induced by HPR.

DETAILED DESCRIPTION OF THE PREFERRED EMBODIMENTS

Figure 1:
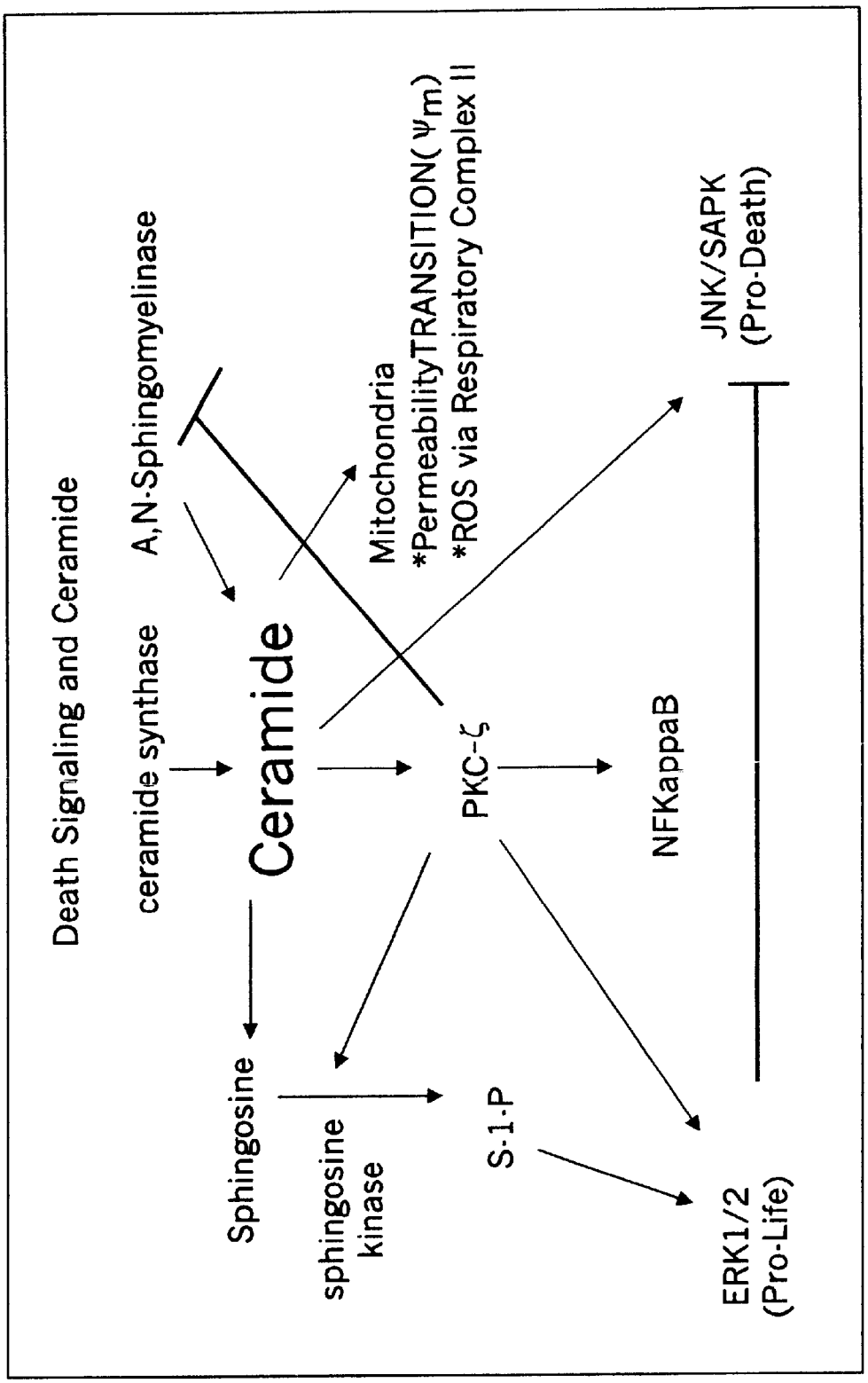
FIG. 1 schematically illustrates ceramide and related pro-death pathways.

The methods of the present invention utilize the combined effects of retinoic acid derivatives and an agent (i.e., a potentiating agent) that manipulates cellular metabolism and cellular control of ceramide-generated toxicity, in order to inhibit or prevent the growth of tumors, cancers, neoplastic tissue and other premalignant and noneoplastic hyperproliferative disorders, all of which are together referred to as hyperproliferative or hyperplastic disorders herein. The treatments employed herein may be used to inhibit growth and/or to induce cytotoxicity (by necrotic or apoptotic mechanisms, or both) in the target cells, which are generally hyperproliferative cells (including tumors, cancers, and neoplastic tissue, along with pre-malignant and non-neoplastic or non-malignant hyperproliferative disorders).

Examples of tumors, cancers, and neoplastic tissue that can be treated by the present invention include but are not limited to malignant disorders such as breast cancers; osteosarcomas; angiosarcomas; fibrosarcomas and other sarcomas; leukemias; lymphomas; sinus tumors; ovarian, uretal, bladder, prostate and other genitourinary cancers, colon esophageal and stomach cancers and other gastrointestinal cancers; lung cancers; myelomas; pancreatic cancers; liver cancers; kidney cancers; endocrine cancers; skin cancers; and brain or central and peripheral nervous (CNS) system tumors, malignant or benign, including gliomas and neuroblastomas.

Examples of premalignant and non-neoplastic or non-malignant hyperproliferative disorders include but are not limited to myelodysplastic disorders; cervical carcinoma-in-situ; familial intestinal polyposes such as Gardner syndrome; oral leukoplakias; histiocytoses; keloids; hemangiomas; hyperproliferative arterial stenosis, inflammatory arthritis; hyperkeratoses and papulosquamous eruptions including arthritis. Also included are viral induced hyperproliferative diseases such as warts and EBV induced disease (i.e., infectious mononucleosis), scar formation, and the like. The methods of treatment disclosed herein may be employed with any subject known or suspected of carrying or at risk of developing a hyperproliferative disorder as defined herein.

As used herein, "treatment" of a hyperproliferative disorder refers to methods of killing, inhibiting or slowing the growth or increase in size of a body or population of hyperproliferative cells or tumor or cancerous growth, reducing hyperproliferative cell numbers, or preventing spread to other anatomic sites, as well as reducing the size of a hyperproliferative growth or numbers of hyperpproliferative cells. As used herein, "treatment" is not necessarily meant to imply cure or complete abolition of hyperproliferative growths. As used herein, a treatment effective amount is an amount effective to result in the killing, the slowing of the rate of growth of hyperproliferative cells, the decrease in size of a body of hyperproliferative cells, and/or the reduction in number of hyperproliferative cells. The potentiating agent (or agents) is included in an amount sufficient to enhance the activity of the first compound, such that the two (or more) compounds together have greater therapeutic efficacy than the individual compounds given alone (e.g., due to synergistic interaction; reduced combined toxicity, etc.).

As used herein, the administration of two or more compounds "in combination" means that the two compounds are administered closely enough in time that the presence of one alters the biological effects of the other. The two compounds may be administered simultaneously (concurrently) or sequentially. Simultaneous administration may be carried out by mixing the compounds prior to administration, or by administering the compounds at the same point in time but at different anatomic sites or using different routes of administration.

The phrases "concurrent administration", "administration in combination", "simultaneous administration" or "administered simultaneously" as used herein, means that the compounds are administered at the same point in time or immediately following one another. In the latter case, the two compounds are administered at times sufficiently close that the results observed are indistinguishable from those achieved when the compounds are administered at the same point in time.

Subjects to be treated by the methods of the present invention include both human subjects and animal subjects for veterinary purposes. Animal subjects are preferably mammalian subjects including horses, cows, dogs, cats, rabbits, sheep, and the like.

A variety of intracellular molecules are known to trigger or inhibit cell death (S. Rowan and D. Fisher, *Leukemia* 11, 457 (1997); K. Saini and N. Walker, *Mol. Cell Biochem.* 178, 9 (1998)). Most current work focuses on elucidating pathways for programmed cell death (apoptosis), in which triggers of apoptosis (such as DNA damage) can activate various pathways (e.g. p53, Fas, and others), which can be modulated by yet other molecules (such as the Bcl-2 family of pro-and anti-apoptotic proteins), with caspase activation being a late step in the final events leading to apoptotic cell death. However, not all cell death occurs via apoptosis, and cell death induced by 4-HPR involves both apoptosis and necrosis (J. Clifford et al., *Cancer Res.* 59, 14 (1999)). The intracellular lipid ceramide is known to mediate apoptosis (L. Obeid et al., *Science* 259, 1769 (1993)(FIG. 1) and necrosis (Guo et al., *Am. J. Physiol.* 276, F390 (1999); Condorelli et al., *Br. J. Pharmacol.* 137, 75 (1999)). It has been shown to cause the apoptosis-inducing permeability transition of mitochondrial membranes (S. Susin et al., *J. Exp. Med.* 186, 25 (1997)), cause apoptosis-inducing ROS generation by mitochondrial complex III inhibition (A. Quillet-Mary et al., *J. Biol. Chem.* 272, 21388 (1997) and activate the pro-death JNK/SAPK pathway (S. Basu et al., *Oncogene* 17, 3277 (1998); T. Okazaki et al., *Cell. Signal.* 10, 685 (1998); W. Jarvis, *Curr. Opin. Oncol.* 10, 552 (1998)). Ceramide also activates a protein kinase (CAPK) (S. Mathias et al., *Biochem. J.* 335(Pt 3), 465 (1998) and a phosphorylase (PP2A) (L. Leoni et al., *Biochem. Pharmacol.* 55, 1105 (1998)) and can lead to the activation of the nuclear transcription factor, NF-kappaB (L. Johns et al., *J.*

Immunol. 152, 5877 (1998); C. Gamard et al., *J. Biol. Chem.* 272, 1682 (1997)). Mechanisms by which cancer cells avoid the cytotoxic effects of ceramide can include metabolism to other forms, including nontoxic glucosylceramide (Y. Lavie et al., *J. Biol. Chem.* 272, 1682 (1997); Y. Lavie et al., *J. Biol. Chem.* 271, 19530 (1996); L. Yong-Yu et al., *J. Biol. Chem.* 274, 1140 (1999)) and sphingosine-1-phosphate. Sphingosine-1-phosphate opposes ceramide-induced cell death by activating the pro-life ERK1/2 pathway (O. Cuvillier et al., *Nature* 381, 800 (1996); O. Cuvillier et al., *J. Biol. Chem.* 273, 2910 (1998)). Thus, modulation of ceramide metabolism offers a means for enhancing the cytotoxic efficacy of 4-HPR (fenretinide) and other ceramide-generating retinoids.

Figure 2:
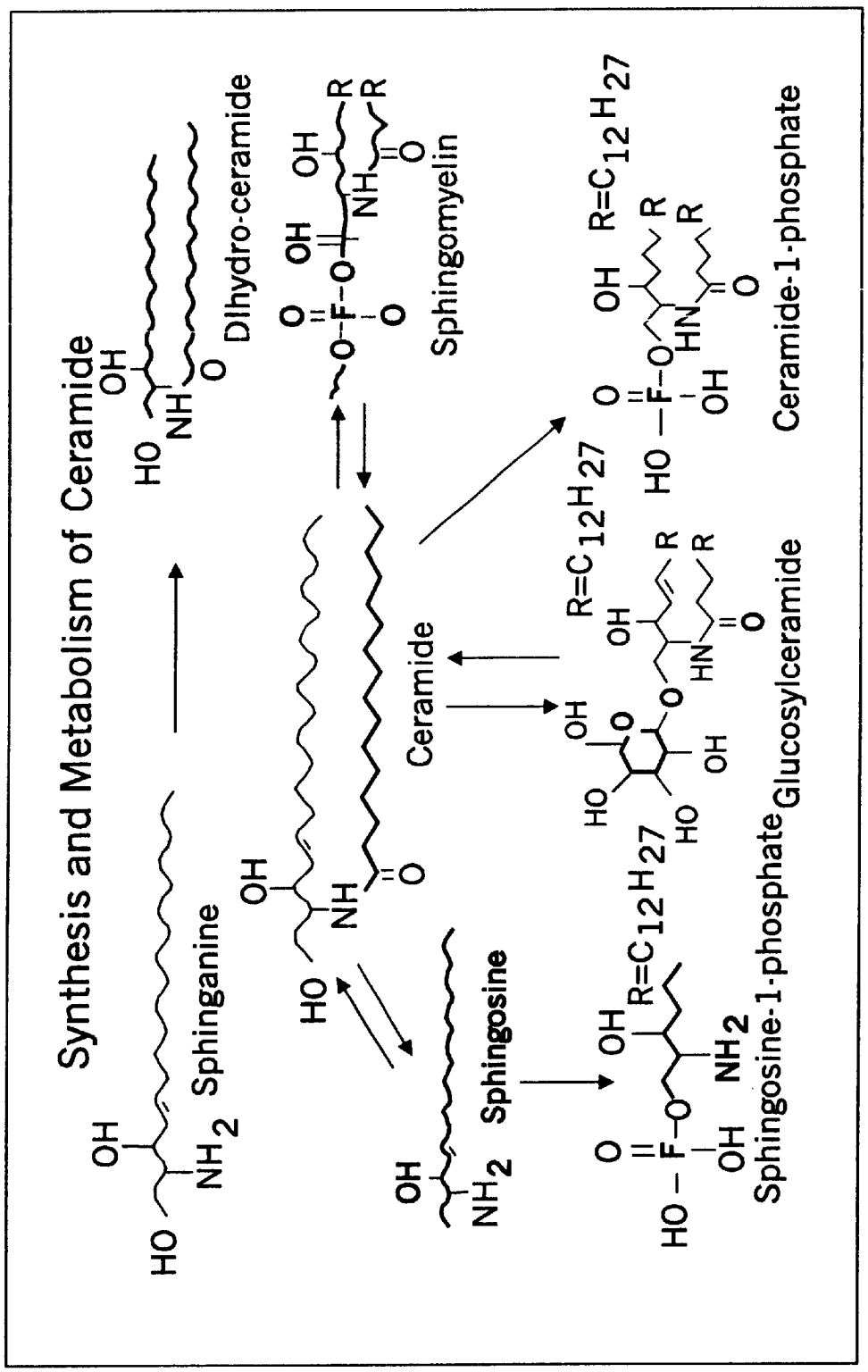
FIG. 2 schematically illustrates metabolic pathways of ceramide.

Some of the key metabolic pathways involved in the synthesis and metabolism of ceramide are shown in FIG. 2. (Y. Hannun, *Science* 274, 1855 (1996). Ceramide is generated intracellularly via activation of (1) ceramide synthase, the de novo synthetic pathway or by activation of the (2) neutral - or acidic-sphingomyelinases, leading to breakdown of sphingomyelin. Ceramide is metabolized to (3) non-cytotoxic glucosylceramide by glucosylceramide synthase; and converted into (4) cytotoxic sphingosine by alkaline- or acidic- ceramidases. Sphingosine is further converted to the anti-apoptotic (5) sphingosine-1-phosphate by sphingosine kinase. We show below that modulation of these pathways can enhance, even synergistically enhance, the cytotoxicity of ceramide-generating retinoids such as 4-HPR (fenretinide).

Compounds that may be used to carry out the present invention, and formulations thereof and the manner of administering the same, are described in detail below.

1. Ceramide-generating Retinoids

Ceramide-generating retinoids or retinoic acid derivatives that can be used to carry out the present invention are those generating ceramide in a host cell to which they are administered and include those described in U.S. Pat. No. 4,190,594 to Gander (the disclosures of all patent references cited herein are incorporated herein by reference). Ceramide-generating retinoids include all trans-retinoic acid (ATRA) and retinoic acid derivatives, including but not limited to:

(A) esters of all-trans-retinoic acid having the following formula:

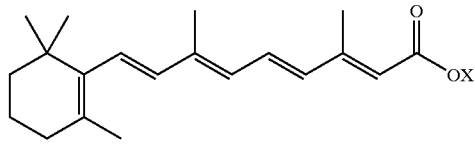

wherein X is a member selected from the group consisting of:

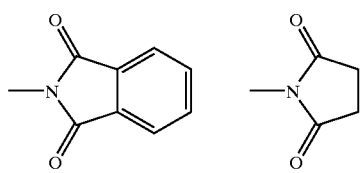

2-cyclohexylethyl; 10-carbomethoxydecyl; 4-hydroxybutyl; cholesteryl; mixed m- and p-vinylbenzyl; and 4-bromobenzyl;

(B) esters of all-trans-retinoic acid having the following formula:

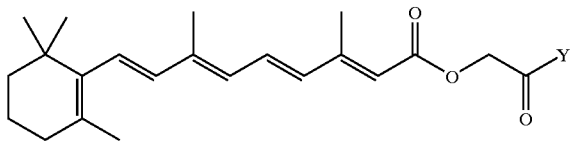

wherein Y is a member selected from the group consisting of: cholesteryloxy; phenyl; 4-bromophenyl; 4-methoxyphenyl; 4-nitrophenyl; 4-hydroxyphenyl; 4-methylphenyl; 4-cyanophenyl; 4-ethoxyphenyl; 4-acetoxyphenyl; 2-naphthyl; 4-biphenyl; 2,5-dimethoxyphenyl; 2,4-dichlorophenyl; 2,4-dimethylphenyl; 3,4-diacetoxyphenyl; 3,4,5-trimethoxyphenyl; and 2,4,6-trimethylphenyl; and (C) amides of all-trans-retinoic acid having the following formula:

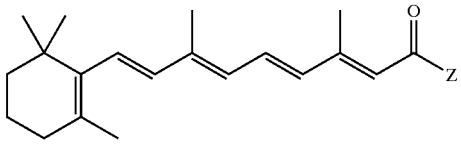

wherein Z is a member selected from the group consisting of: n-propylamino; tert-butylamino;1,1,3,3-tetramethylbutylamino; 1-morpholino; 4-hydroxyphenylamino, 4-carbomethoxy-2-hydroxyphenylamino; beta-(3,4-dimethoxyphenyl)-ethylamino; 2-benzothiazolylamino; 1-imidazolyl; 1-(2-nicotinoylhydrazolyl); 1-benzotriazolyl; 1-(1,2,4-triazolyl);

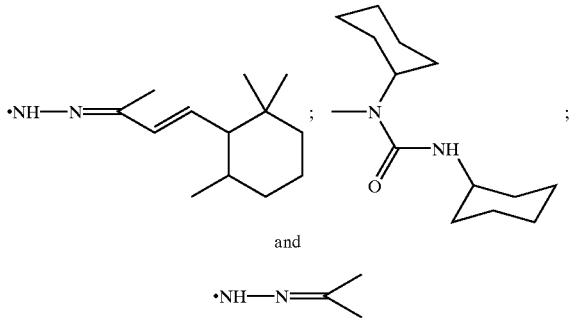

and

Particularly preferred is all-trans-N-(4-hydroxyphenyl) retinamide, also called fenretinide, which has CAS registry number 65646-68-6, and has the structure:

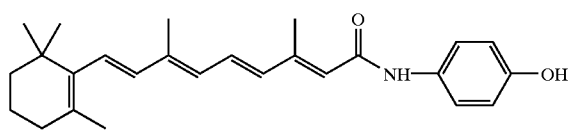

The foregoing compounds can be prepared in accordance with known techniques. See, e.g., U.S. Pat. No. 4,190,594 to Gander et al.; U.S. Pat. No. 4,665,098 to Gibbs.

Additional retinoic acid derivatives that can be used to carry out the present invention include C-Glycoside analogs of N-(4-hydroxyphenyl)retinamide-O-glucuronide. Such compounds and their preparation are known and described in U.S. Pat. Nos. 5,663,377 and 5,599,953, both to Curley et al., the disclosures of which are incorporated by reference herein in their entirety. Such compounds may have the general formula:

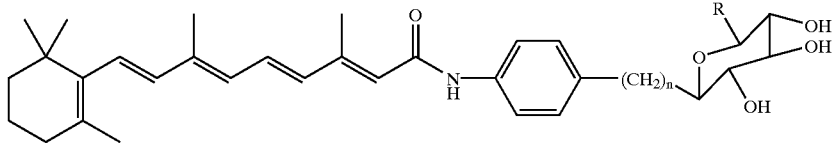

where R is COOH, CH$_2$OH, or H, and n is 0 or 1.

Specific examples of such compounds include: 4-(retinamido)phenyl-C-glucuronide; 4-(retinamido)phenyl-C-glucoside; 4-(retinamido)phenyl-C-xyloside; 4-(retinamido)benzyl-C-glucuronide; 4-(retinamido)benzyl-C-glucoside; 4-(retinamido)benzyl-C-xyloside; 1-(β-D-glucopyranosyl) retinamide; and 1-(D-glucopyranosyluronosyl) retinamide.

2. Glucosylceramide Synthesis and 1-acylceramide Synthesis Inhibitors

Any compound that inhibits glycosylceramide synthesis and/or a 1-acylceramide synthesis inhibitor can be used, Glucosylceramide synthase inhibitors and/or 1-acylceramide synthase inhibitors are preferred. By "and/or" is meant that either of two drugs with a selective activity for one or the other enzyme may be administered singly or in combination, or a single drug active in inhibiting both enzymes may be given. Examples of such compounds include, but are not limited to, compounds having the formula:

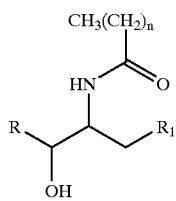

where R is an aromatic ring such as phenyl, a cyclohexyl group, or an alpiphatic group having 10 to 15 carbon atoms, R$_1$ is an amine group such as a morpholino group; and n is an integer of from 4 to 18 (including functional homologues, isomers and pharmaceutically acceptable salts thereof. Preferably, n is 4, 6, 8, 10, 12 or 14, and the D enantiomer of such compounds are preferred. Such compounds are known and are disclosed, for example, in U.S. Pat. No. 5,302,609 to Shayman and Radin; U.S. Pat. No. 5,041,441 to Radin et al.; and U.S. Pat. No. 5,707,649 to Inokuchi al. Specific examples of glucosylceramide synthase inhibitors include:

1-phenyl-2-acylamino-3-morpholino-1-propanol in which n is 6 to 12;

1-phenyl-2-decanoylamino-3-morpholino-1-propanol (PDMP);

1-phenyl-2-palmitoylamino-3-morpholino-1-propanol (PPMP); and

Tamoxifen, including tamoxifen citrate.

3. Sphingosine-1-phosphate Synthesis Inhibitors.

Any sphingosine-1-phosphate synthesis inhibitor can be used to carry out the present invention, with sphingosine kinase inhibitors such as D-erythro-N,N-dimethylsphingosine currently preferred. Additional sphingosine kinase inhibitors are known. For example, the compound may be Sankyo Co. sphingosine kinase inhibitor F12509A (or a pharmaceutically acceptable salt thereof, disclosed in Japanese Patent Application 9176083 (1997) and having the structure:

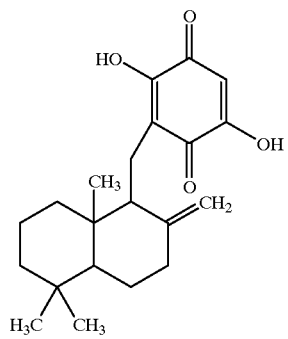

4. Protein Kinase C Inhibitors

Example protein kinase C inhibitors include those described in U.S. Pat. No. 4,816,450 to Bell et al. Such compounds include those having the general formula:

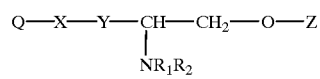

wherein Q is CH$_3$—(CH$_2$)$_n$— or CH$_3$—(CH$_2$)$_m$—CH=CH—(CH$_2$)$_p$— wherein n is 2–30, m is 1–15 and p is 1–15;

wherein X is —CH$_2$—CH$_2$— or —CH=CH—, or such substituted by one or more halogens or C$_1$–C$_3$ alkyl groups;

wherein Y is —C(—OH)H—, —C(=O)—, —C(—SH)H—, —CH$_2$—, or —C(—W)H—; wherein W is halogen (the term "halogen" as used herein refers to fluorine, chlorine, bromine, iodine, etc.);

wherein R$_1$ and R$_2$ are the same or different and are selected from hydrogen, lower alkyl groups having from 1 to 7 carbon atoms, aralkyl, and aryl groups; and wherein Z is selected from the group consisting of phosphate, H, galactosyl, sulfogalactosyl, glucosyl, lactosyl, trihexosyl, phosphorylcholine, GalNAc-Gal-Glc, Gal-Gal-Glc, Sia-Gal-Glc,

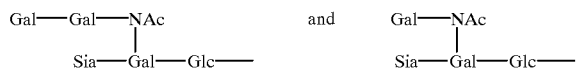

Preferred are dihydrosphingosine and the isomers D, L, or DL-threo-dihydrosphingosine. Most preferred is L-threo-dihydrosphingosine, also known as (2S,3S)-2-amino-1,3- octadecanediol or safingol. These compounds may be prepared as emulsions for administration as described in U.S. Pat. No. 5,677,341 to Lyons.

Note that not all protein kinase C inhibitors are necessarily active, depending upon the specific PKC subtypes that are inhibited thereby. The staurosporine derivative UCN01 is not active in the present invention, indicating that the inhibitor should inhibit subtypes not inhibited by this compound, or should inhibit them to a greater extent than UCN01. It is presently believed that PKC inhibitor should be selected so that protein kinase C zeta is inhibited thereby.

It is not excluded that safingol performs a function(s) contributory to the function of the present invention that is distinct from PKC inhibition. Therefore, safingol, and other compounds which perform this function(s), are active in the present invention and included therein, without binding applicants to a particular underlying theory of the invention.

5. Additional Active Compounds and Screening

Additional active compounds can be generated by known techniques, including rational drug design techniques and/or random drug design techniques (or combinatorial chemistry techniques).

In active compounds that interact with a receptor, the interaction takes place at the surface-accessible sites in a stable three-dimensional molecule. By arranging the critical binding site residues in an appropriate conformation, compounds which mimic the essential surface features of the active compound binding region may be designed and synthesized in accordance with known techniques. A molecule which has a surface region with essentially the same molecular topology to the binding surface of the active compound will be able to mimic the interaction of the active compound with its corresponding receptor. Methods for determining the three-dimensional structure of active compounds and producing active analogs thereof are known, and are referred to as rational drug design techniques. See, e.g., U.S. Pat. No. 5,593,853 to Chen; U.S. Pat. Nos. 5,612,895 and 5,331,573 to Balaji et al.; U.S. Pat. No. 4,833,092 to Geysen; U.S. Pat. No. 4,859,765 to Nestor; U.S. Pat. No. 4,853,871 to Pantoliano; and U.S. Pat. No. 4,863,857 to Blalock (the disclosures of all U.S. Patent references cited herein are to be incorporated herein by reference).

In combinatorial chemistry (or random drug design) techniques, large combinatorial libraries of candidate compounds are screened for active compounds therein. Libraries used to carry out the present invention may be produced by any of a variety of split synthesis methods. Split synthesis methods in which a releasable tag is attached to the particle along with the organic compounds of interest are also known as cosynthesis methods. A variety of such methods are known. See, e.g., A. Furka et al., *J. Pept. Protein Res.* 37, 487 (1991); K. Lam et al., *Nature* 354, 82 (1991); R. Zuckermann et al., *Int. J. pept. Protein Res.* 40, 498 (1992); F. Sebestyen et al., *Bioorg. Med. Chem. Lett.* 3, 413 (1993); K. Lam et al., *Bioorg. Med. Chem. Lett.* 3, 419 (1993). For example, the library may be a library of organometallic compounds wherein the compound is a metal-ligand complex. The metal in the complex may be an early or late transition metal in high, low or zero oxidation states. The metal may also be any of the main group metals, alkali metals, alkaline earths, lanthanides or actinides. The ligand in the metal-ligand complex may be composed of, or derived from, chiral or achiral forms of cyclopentadienes, amino esters, oxazolidoinones, hydroxy acids, hydroxy esters, hydroxy amides, pyridines, fused pyridines, nitrogen heterocycles, oxazoles, imidazoles, pyrroles, crown ethers, cryptands, carcerands, phosphines, diphosphines, polyphosphines, quinuclidines, quinines, alkaloids, dextrins, cyclodextrins, salens, porpyrins, biaryls, sulfonamides, Schiff bases, metallocenes, monools, diols, polyols, amines, diamines, polyamines, ammonium salts, peptides, proteins, nucleic acids, etc.

As a second example, the library may be a library of non-metal compounds including, but not limited to, chiral or achiral forms of cyclopentadienes, amino esters, oxazolidinones, hydroxy acids, hydroxy esters, hydroxy amides, pyridines, fused pyridines, nitrogen heterocycles, oxazoles, imidazoles, pyrroles, crown ethers, cryptands, carcerands, phosphines, diphosphines, polyphosphines, quinuclidines, quinines, alkaloids, dextrins, cyclodextrins, salens, porphyrins, biaryls, sulfonamides, Schiff bases, metallocenes, monools, diols, polyols, amines, diamines, polyamines, ammonium salts, peptides, proteins, nucleic acids, etc.

The solid supports may be separate from one another, or may be discreet regions on a surface portion of a unitary substrate, which surface portion may be positioned at the interface so that a plurality of the discreet regions are positioned at the interface. Such "chip-type" or "pin-type" solid supports are known. See, e.g., U.S. Pat. No. 5,288,514 to Ellman (pin-based support); U.S. Pat. No. 5,510,270 to Fodor et al. (chip-based support). Separate discreet supports (e.g., particles or beads) are currently preferred. Synthesis of the catalyst library and linking thereof to the discreet solid support may be carried out in accordance with known techniques, such as described in U.S. Pat. No. 5,565,324 (the disclosure of which is incorporated by reference herein in its entirety), or variations thereof that will be apparent to those skilled in the art.

Compounds selected by any means, including but not limited to those described above, may be screened for activity in increasing, including additively and synergistically increasing but preferably synergistically increasing, the cytostatic or cytotoxic activity of a ceramide-generating retinoid in tumor cells (or other hyperproliferative cells), by a method comprising:

(a) contacting first control tumor cells with an amount of ceramide-generating retinoid (e.g., an amount that may or may not itself be effective to inhibit growth of said tumor cells);

(b) contacting second control tumor cells with an amount of a test compound (eg., an amount that may or may not itself be effective to inhibit growth of said tumor cells); and (c) contacting experimental tumor cells with both said amount of ceramide generating retinoid in step (a) above and said amount of a test compound in step (b) above; and (d) determining the growth inhibition of said tumor cells of steps (a), (b) and (c) above; and then (e) comparing the growth inhibition or cytotoxic activity in the experimental tumor cells of step (c) with the growth inhibition of the control tumor cells of steps (a) and (b), a greater degree of growth inhibition determined in the experimental tumor cells of step (c) than the combined growth inhibition of the control tumor cells of steps (b) and (c) indicating that the test compound enhances the activity of the ceramide-generating retinoid.

The comparing step may be carried out by any suitable means, such as by calculating a Combination Index, where a value less than 1 (e.g., less than 0.9) indicates the compounds are synergistic. Any tumor cells can be used, including but not limited to neuroblastoma, lung, melanoma, prostate, leukemia, colon, breast, and pancreas tumor cells. Any ceramide-generating retinoid such as fenretinide can be used. Other hyperproliferative cells including pre-malignant and non-malignant cells can be used instead of tumor cells, as noted with respect to conditions for treatment above. In preferred embodiments, the test compound is a ceramide-degradation inhibitor, or other agent that manipulates cellular metabolism or cellular control of ceramide-generated cytotoxicity. The determining step may be carried out by looking for growth inhibition or cytotoxicity in general, or by particularly determining necrosis, apoptosis, or both. The method may be used to identify active compounds that are ceramide-degradation inhibitors, other compounds that manipulate cellular metabolism or cellular control of ceramide-generated cytotoxicity, or compounds that operate by still other mechanisms in addition to those described herein.

Compounds (including the pharmaceutically acceptable salts thereof) that have not previously been known as useful in a method of treating hyperproliferative diseases in combination with a ceramide-generating retinoid, can be prepared, formulated and used in the methods described herein in addition to, or in alternative to, the ceramide-degradation inhibitors described herein. Depending upon the compounds selected for screening, such compounds may be novel compounds, may be known compounds but not previously known for a medicinal or pharmaceutical use, may be compounds previously known for a medicinal or pharmaceutical use but not previously known for use in combination with a ceramide-generating retinoid as described herein.

6. Formulations and Administration

The active compounds described above may be formulated for administration in a single pharmaceutical carrier or in separate pharmaceutical carriers for the treatment of a variety of conditions. In the manufacture of a pharmaceutical formulation according to the invention, the active compounds including the physiologically acceptable salts thereof, or the acid derivatives of either thereof are typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.5% to 95% by weight of the active compound. One or more active compounds may be incorporated in the formulations of the invention, which may be prepared by any of the well known techniques of pharmacy consisting essentially of admixing the components, optionally including one or more accessory ingredients.

The formulations of the invention include those suitable for oral, rectal topical, buccal (e.g., sub-lingual), vaginal, parenteral (e.g., subcutaneous intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the active compound in a flavoured base, usually sucrose and acacia or tragacanth; and pastilles comprising the compound in an inert base such as gelatin and glycerin or sucrose and acacia.

Formulations of the present invention suitable for parenteral or vaginal administration conveniently comprise sterile aqueous preparations of the active compound, which preparations are preferably isotonic with the blood of the intended recipient. These preparations may be administered by means of subcutaneous, intravenous, intramuscular, or intradermal injection. Such preparations may conveniently be prepared by admixing the compound with water or a glycine buffer and rendering the resulting solution sterile and isotonic with the blood.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include vaseline, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. Suitable formulations comprise citrate or bis\tris buffer (pH 6) or ethanol/water and contain from 0.1 to 0.2M active ingredient.

As noted above, the present invention provides pharmaceutical formulations comprising the active compounds (including the pharmaceutically acceptable salts thereof, in pharmaceutically acceptable carriers for oral, rectal, topical, buccal, parenteral, intramuscular, intradermal, or intravenous, and transdermal administration.

The therapeutically effective dosage of any one active agent, the use of which is in the scope of present invention, will vary somewhat from compound to compound, patient to patient, and will depend upon factors such as the condition of the patient and the route of delivery. Such dosages can be determined in accordance with routine pharmacological procedures known to those skilled in the art, particularly in light of the disclosure provided herein.

For fenretinide, for systemic treatment, a dose to achieve a plasma level of about 1, 2, or 3 µM to 10 or 20 µM will be employed; typically (for oral dosing) 50 or 100 to 500 or 1000, 2000 or 3000 mg/m² body surface area per day.

For tamoxifen, a serum level of 1.5 to 2 µM achieves a clinically desireable effect, and these levels can be achieved at a dosage of about 150 to 300 or 500 mg/day of tamoxifen citrate P.O, or at 300 or 400 to 500 or 700 mg/m² per day. These levels are achievable on a pulse-dose basis using higher P.O. dosing of 400–500 mg/day.

Safingol is administered to achieve peak serum levels of about 1 to 10 µM e.g., 7.5), or dosages of 5 or 10 to 30 or 40 mg/kg (e.g., 20 mg/kg).

The present invention is explained in greater detail in the following non-limiting examples.

EXAMPLE 1

Cytotoxicity Assay

Cytotoxicity is determined using the DIMSCAN assay system (R. Proffitt et al., *Cytometry* 24, 204–213 (1996); T. Frgala et al., *Proc. AACR*, 36, 303 (1995). The system employs digital imaging microscopy to quantify viable cells, which selectively accumulate fluorescein diacetate to become brightly fluorescent. The system is capable of measuring cytotoxicity over a 4–5 log dynamic range by quenching the residual fluorescence of dead and dying cells with eosin Y and quantifying the total fluorescence of viable cells using digital thresholding. Measured fluorescence is directly proportionate to the number of viable cells. A comparison of the total fluorescence of a drug-treated cell population to the fluorescence of a similar number of untreated cells yields a survival fraction. In brief, 5000 to 10,000 SK-N-RA neuroblastoma cells/well are replicate plated into 60 wells of a 96-well tissue culture plate in 0.1 cc media and allowed to attach overnight. Drug(s) are then added in 0.05 cc media to the final concentrations indicated. There are 12 wells treated per drug concentration. Twelve wells receive drug-vector only to the appropriate final concentration and serve as controls for the plate. Cells are incubated for 96–120 hours at 37° C. in 5% $CO_2$. Fluorescein diacetate is then added to each well in 0.05 cc media to a final concentration of 8 microgram/cc. Cells are incubated for a further 15 minutes at 37° C. and 0.03 cc of 0.5% eosin Y is added to each well. Total fluorescence of viable cells is then measured by digital imaging microscopy.

EXAMPLE 2

Ceramide Assay

The ceramide assay is carried out as follows. 500,000 neuroblastoma cells/well are replicate plated in six-well tissue culture plates and allowed to attach overnight. Tritiated (3H)-palmitic acid (a lipid precursor) is added to 1 microcure/cc and fenretinide added to a final concentration of 10 uM. Control cells receive tritiated label but no drug. At the indicated time, cells are harvested from triplicate wells, washed, and lipids extracted with methanol, acetic acid, water, and chloroform. The organic layer (containing the tritium label incorporated into lipids) is isolated and dried down by a nitrogen stream. The lipid sample is dissolved in chloroform: methanol and 10% of each sample assayed to estimate the total tritium in the lipid sample. The lipids in sample fractions, together with unlabeled ceramide standards, are then separated by thin layer chromatography and the plates developed by iodine vapor. The region of the plate corresponding to the ceramide standard is scraped and the tritium of the co-migrating sample ceramide is measured. Total sample ceramide is then expressed as percent tritium label in ceramide versus tritium in total lipid.

EXAMPLES 3–9

Cytotoxicity and Ceramide Studies

Examples 3 to 9 are illustrated by FIGS. 1 to 9 herein, respectively. These examples were carried out with the procedures generally described in Examples 1 and 2 above.

Figure 3:
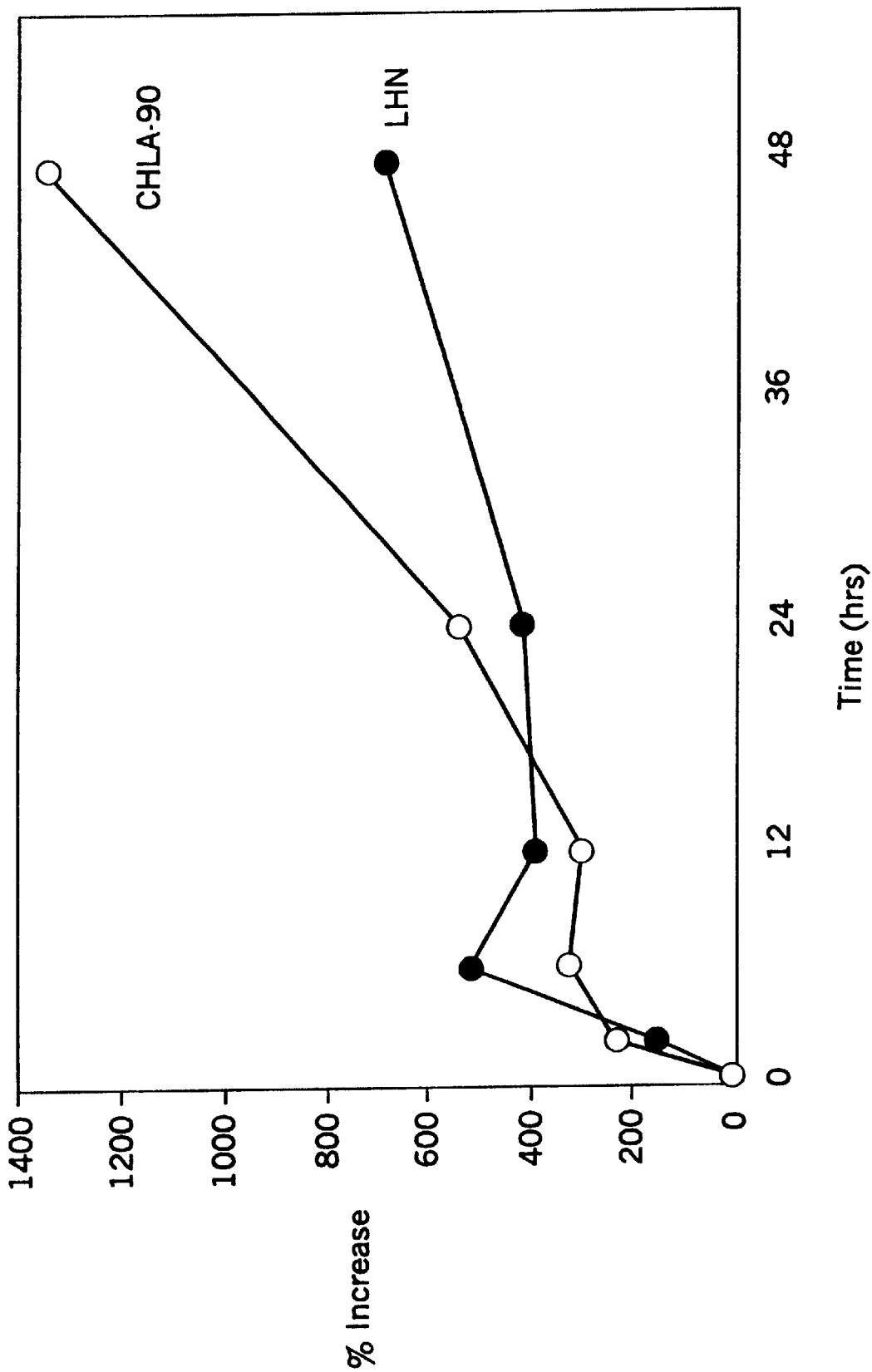
FIG. 3 illustrates the effect of 10 $\mu$M fenretinide (labeled HPR or H) on ceramide generation in the drug sensitive neuroblastoma cell line SMS-LHN (filled circles) and on the alkylating agent and etoposide neuroblastoma cell line CHLA-90 (open circles).

FIG. 3 illustrates the effect of 10 µM fenretinide (labeled HPR or H) at 20% $O_2$ on ceramide generation in the drug sensitive neuroblastoma cell line SMS-LHN (filled circles) and on the drug resistant neuroblastoma cell line CHLA-90 (open circles). Note that both cell lines were found to generate ceramide in response to fenretinide.

Figure 4:
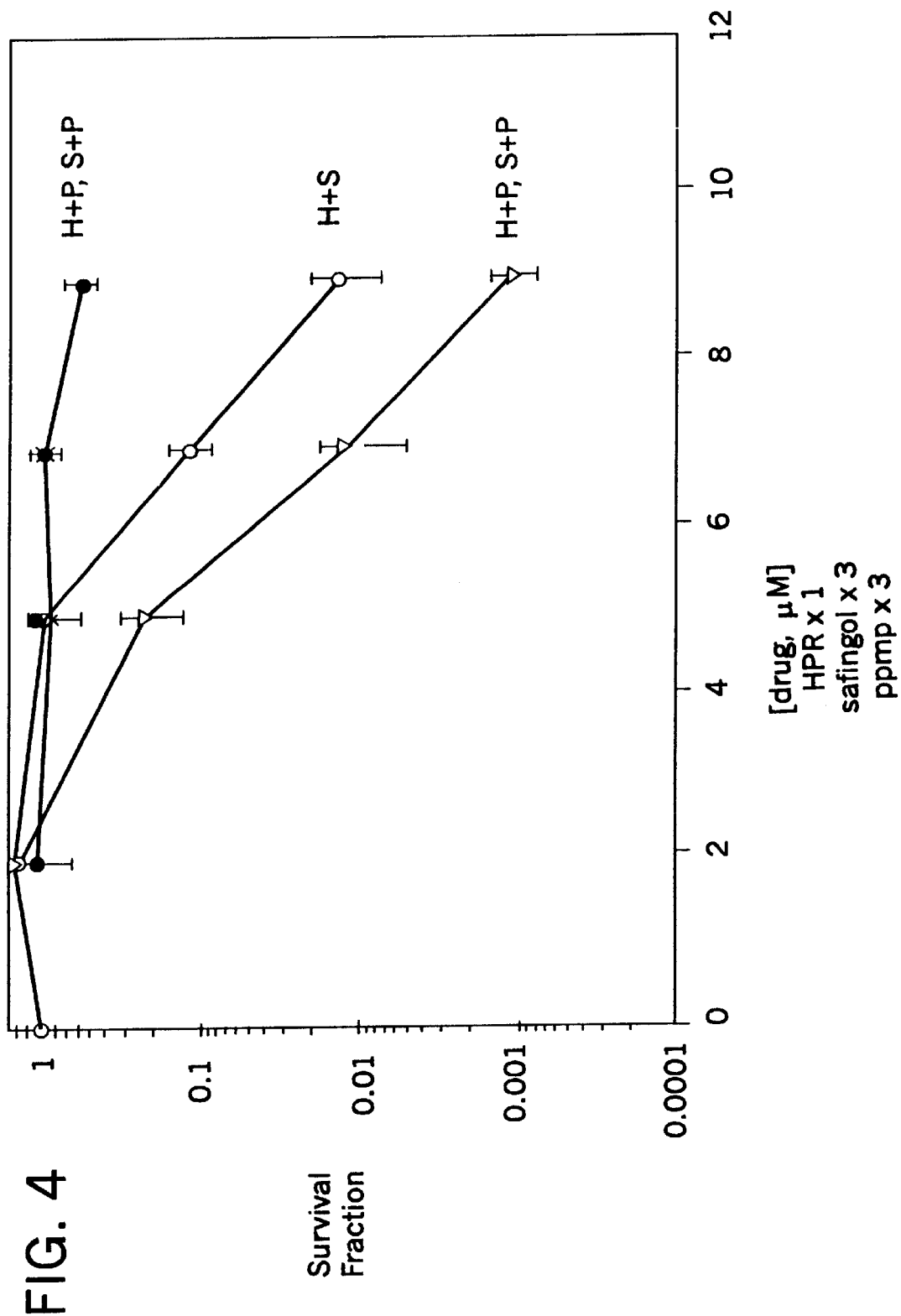
FIG. 4 illustrates the effect of various combinations of fenretinide (HPR; H), L-threo-dihydrosphingosine (safingol; S), a protein kinase C inhibitor and 1-phenyl-2-palmitoylamino-3-morpholino-1-propanol (PPMP; P), a glucosylceramide synthase inhibitor, on cell survival in a highly HPR resistant cell line (SK-N-RA), at varying concentrations. Filled circles represent the combination of safingol and ppmp; open circles represent the combination of fenretinide and safingol; filled triangles represent the combination of fenretinide and ppmp; open triangles represent the combination of fenretinide, safingol and ppmp. Dosages are as indicated on the horizontal axis.

FIG. 4 illustrates the effect of various combinations of fenretinide (HPR; H), L-threo-dihydrosphingosine (safingol; S), a protein kinase C inhibitor and 1-phenyl-2-palmitoylamino-3-morpholino-1-propanol (ppmp; P), a glucosylceramide synthase inhibitor, on cell survival in a highly resistant cell line (sk-N-RA), at varying concentrations, at 20% $O_2$. Note the combined effects of the drugs. Filled circles represent the combination of safingol and ppmp; open circles represent the combination of fenretinide and safingol; filled triangles represent the combination of fenretinide and ppmp; open triangles represent the combination of fenretinide, safingol and ppmp. Dosages are as indicated on the horizontal axis.

Figure 5:
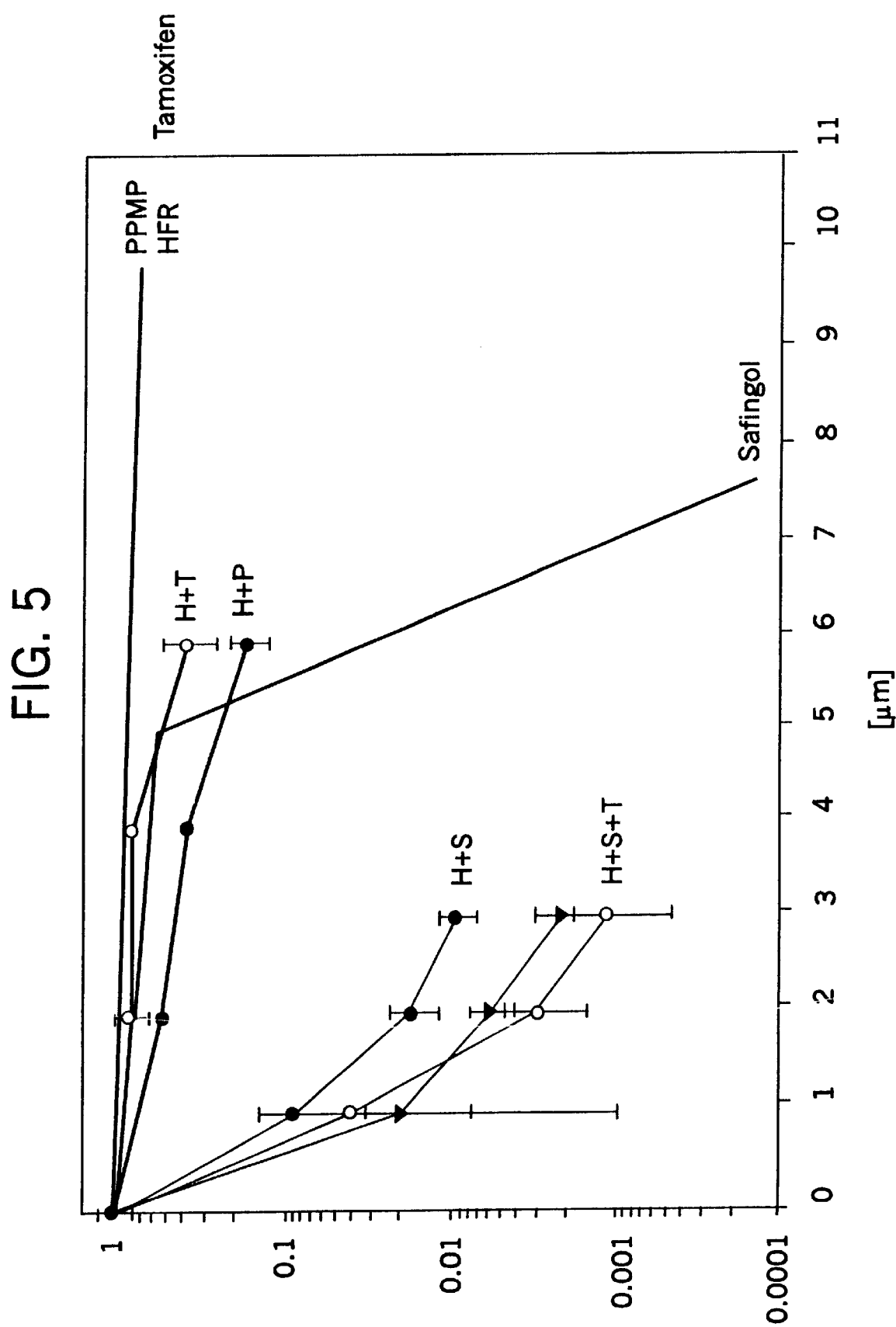
FIG. 5 illustrates the effect of various compound combinations with dosages varrying as indicated, but at a fixed 10 $\mu$M dose of fenretinide, on the survival of SK-N-RA cells. T or Tamoxifen refers to tamoxifen citrate. Filled circles labelled H+P represent fenretinide plus ppmp; open circles labelled H+T represent fenretinide plus tamoxifen; filled circles labelled H+S represent fenretinide plus safingol; open circles H+S+T represent fenretinide plus safingol and tamoxifen (1:1); filled trinagles represent fenretinide plus 3 $\mu$M tamoxifen fixed plus safingol. Other dosages are as indicated on the horizontal axis.

FIG. 5 illustrates the effect of various compound combinations with dosages varrying as indicated, but at a fixed 10 µM dose of fenretinide, on the survival of SK-N-RA cells at 20% 02. T or Tamoxifen refers to tamoxifen citrate. Note the low cytotoxicity for individual compounds, but the high cytotoxicity for combinations of compounds. Filled circles labelled H+P represent fenretinide plus ppmp; open circles labelled H+T represent fenretinide plus tamoxifen; filled circles labelled H+S represent fenretinide plus safingol; open circles H+S+T represent fenretinide plus safingol and tamoxifen (1:1); filled triangles represent fenretinide plus 3 µM tamoxifen fixed plus safingol. Other dosages are as indicated on the horizontal axis.

Figure 6:
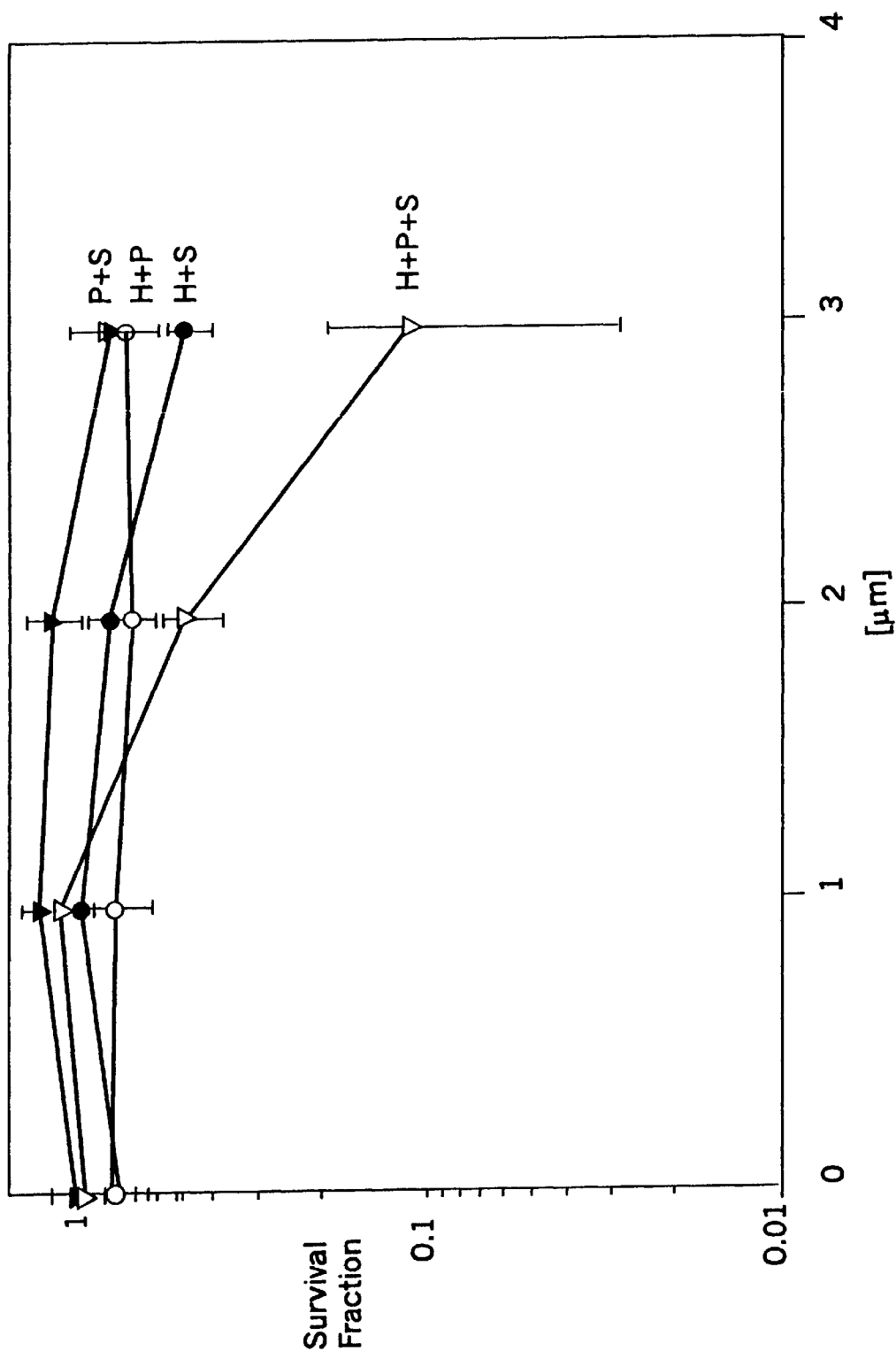
FIG. 6 shows the activity of low dosage fenretinide in combination with other compounds on the survival fraction of SK-N-RA cells. Filled circles represent 3.3 $\mu$M fenretinide plus safingol; open circles represent 3.3 $\mu$M fenretinide plus PPMP; filled triangles represent PPMP plus safingol (1:1) without fenretinide; open triangles represent 3.3 $\mu$M fenretinide plus PPMP plus safingol (1:1). Other dosages are as indicated on the horizontal axis.
Figure 7:
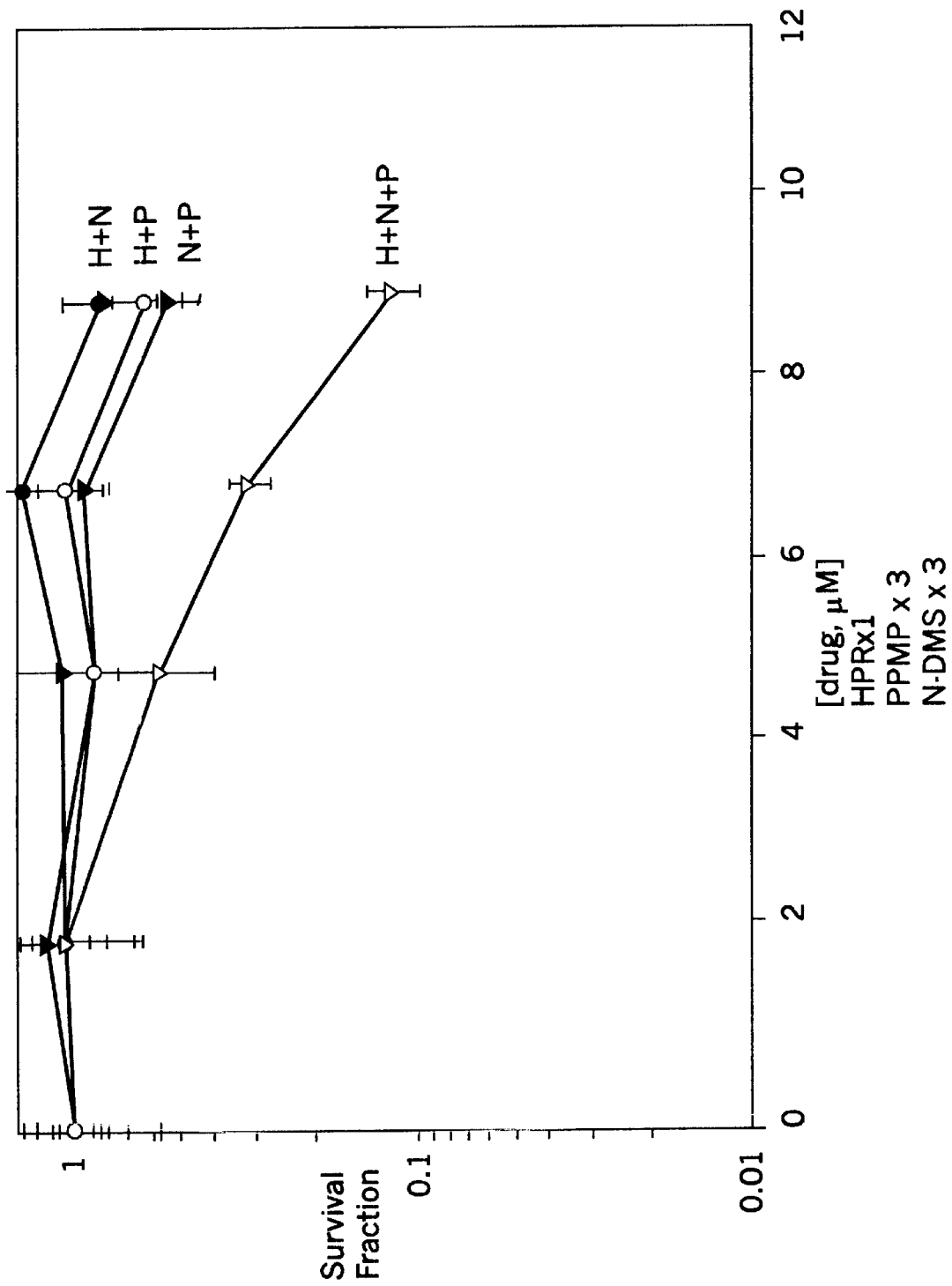
FIG. 7 shows the effect of various drug combinations on the survival fraction of SK-N-RA cells. N-DMS (or N) refers to d-erythro-N,N-dimethylsphingosine, a sphingosine kinase inhibitor. Filled circles represent N-DMS plus ppmp; open circles represent fenretinide plus ppmp; filled triangles represent fenretinide plus N-DMS; open triangles represent fenretinide plus N-DMS plus ppmp. Dosages are as indicated on the horizontal axis.

FIG. 6 shows the activity of low dosage fenretinide in combination with other compounds on the survival fraction of SK-N-RA cells at 20% O2. Filled circles represent 3.3 µM fenretinide plus safingol; open circles represent 3.3 µM fenretinide plus ppmp; filled triangles represent ppmp plus safingol (1:1) without fenretinide; open triangles represent 3.3 µM fenretinide plus ppmp plus safingol (1:1). Other dosages are as indicated on the horizontal axis FIG. 7 shows the effect of various drug combinations on the survival fraction of sk-N-RA cells at 20% $O_2$. N-DMS (or N) refers to d-erythro-N,N-dimethylsphingosine, a sphingosine kinase inhibitor. Filled circles represent N-DMS plus PPMP; open circles represent fenretinide plus ppmp; filled triangles represent fenretinide plus N-DMS; open triangles represent fenretinide plus N-DMS plus PPMP. Dosages are as indicated on the horizontal axis.

Figure 8:
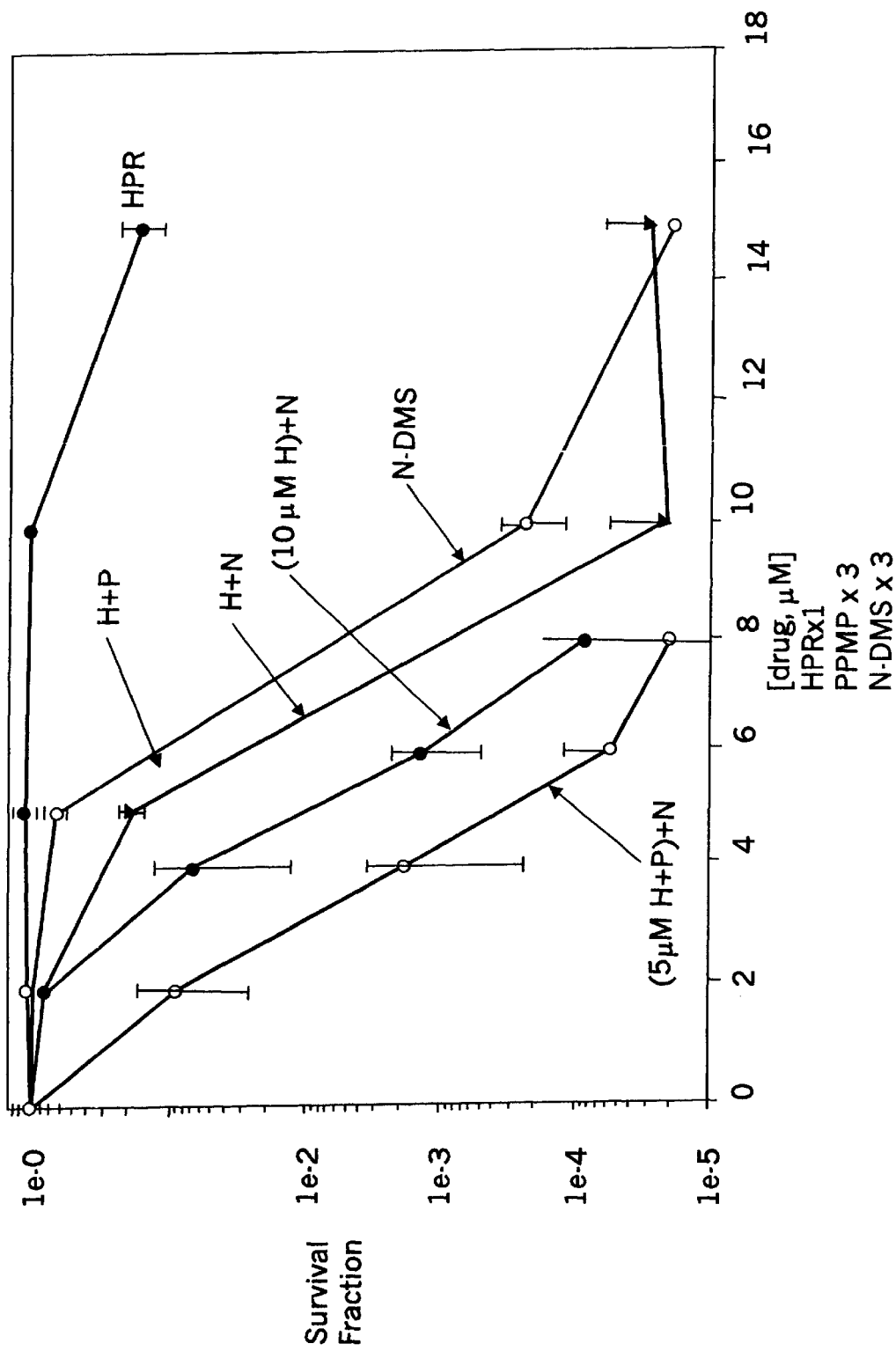
FIG. 8 illustrates the activity of various drug combinations on the survival of SK-N-RA cells. Filled circles labelled HPR represent fenretinide; open circles labelled N-DMS represent N-DMS; filled triangles represent HPR plus N-DMS; filled circles labelled 10 $\mu$M H+N represent a 10 $\mu$M fixed dose of fenretinide plus N-DMS; open circles labelled 5 $\mu$M H+P+N represent 5 $\mu$M fenretinide fixed dose plus 5 $\mu$M ppmp fixed dose plus N-DMS. The solid line represents fenretinide plus ppmp. Dosages are fixed where so indicated; otherwise dosages are as shown on the horizontal axis.

FIG. 8 illustrates the activity of various drug combinations on the survival of sk-N-RA cells at 20% $O_2$. Filled circles labelled HPR represent fenretinide; open circles labelled N-DMS represent N-DMS; filled triangles represent HPR plus N-DMS; filled circles labelled 10 µM H+N represent a 10 µM fixed dose of fenretinide plus N-DMS; open circles labelled 5 µM H+P+N represent 5 µM fenretinide fixed dose plus 5 µM PPMP fixed dose plus N-DMS the solid line represents fenretinide plus PPMP. Dosages are fixed where so indicated; otherwise dosages are as shown on the horizontal axis. Note the increased cytotoxicity when N-DMS is added to fenretinide and PPMP.

Figure 9:
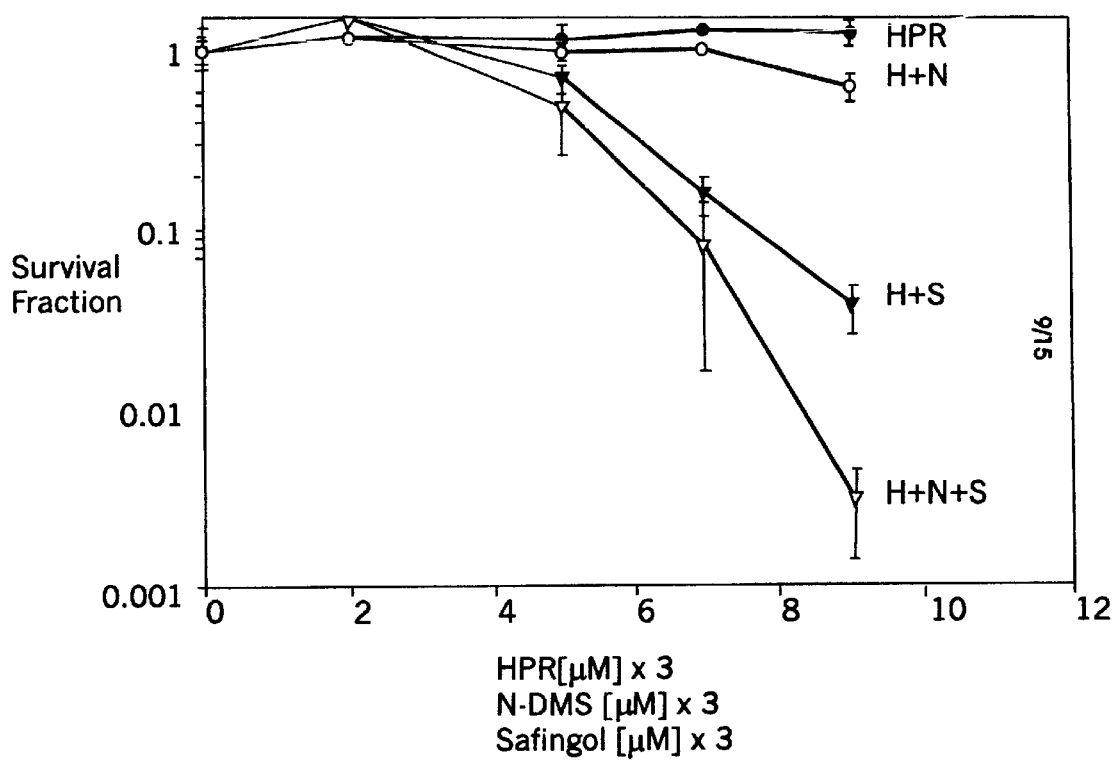
FIG. 9 illustrates the activity of drug combinations on the survival of SK-N-RA cells. Filled circles represent fenretinide; open circles represent fenretinide plus N-DMS (3:1); filled triangles represent fenretinide plus safingol (3:1); open triangles represent fenretinide plus N-DMS plus safingol (3:1:1). Dosages are as indicated on the horizontal axis.

FIG. 9 illustrates the activity of drug combinations on the survival of sk-N-RA cells at 20% $O_2$. Filled circles represent fenretinide; open circles represent fenretinide plus N-DMS (3:1); filled triangles represent fenretinide plus safingol (3:1); open triangles represent fenretinide plus N-DMS plus safingol (3:1:1). Dosages are as indicated on the horizontal axis. Note the cytotoxicity of the three drug combination.

EXAMPLE 10

All Compounds Need Not Be Co-Present for the Entire Treatment Period

In some cell lines, we have demonstrated that safingol need only be co-present with HPR for a portion of the entire treatment period in order to obtain an increase in anti-tumor cell activity. In these experiments, safingol and HPR were added together at Time=0. Then, at various times, the cell culture medium containing both drugs was removed and replaced with medium that contained a similar concentration of HPR-only. Cells were then allowed to complete 96–120 hour incubations and their survival compared to cells that had been exposed to both drugs for the entire 96–120 hours as previously described. The results demonstrate that safingol need not be co-present with HPR for the entire HPR treatment period in order for the invention to increase tumor cell kill compared to HPR treatment alone. In some instances, co-presence of Safingol and HPR for less than 12 hours of the entire 96–120 hour HPR treatment period was sufficient to obtain a large fraction of the total increase in cell kill the invention caused. This demonstrates that all compounds claimed in the invention need not be co-present at all times in order for the invention to function.

Methods. Cells were added in 100 μL of whole medium per well to 96-well microplates for DIMSCAN cytotoxicity assays as previously described. Cell lines used included the neuroblastoma cell lines CHLA-90 and SK-N-RA, and the lung carcinoma cell line,. A549. At time=+0, HPR and safingol were added, to the final drug concentrations listed, in 50 μL of whole medium per well (a final total of 150 μL medium per well). Also at time=+0, the same concentration of HPR, as a single agent, was added in 50 μL of whole medium to the wells of a duplicate plate (to a final total of 150 μL medium per well). Plates were incubated at 37° C. At the times listed, the 150 μL of medium in each of 12 wells from a HPR+safingol plate was removed, discarded, and replaced with 150 μL of medium from 12 wells from an HPR-only plate ('pre-equilibrated medium'). The medium of the wells of the HPR+safingol plate was replaced with the 'pre-equilibrated medium', rather than adding new HPR in fresh medium, to simulate any possible conditioning of the medium or HPR-degradation that may have occurred with time in the original two-drug wells. The plate was reincubated and assayed for cytotoxicity by DIMSCAN assay at +96–120 hours as indicated. The final data point on each graph represents the survival fraction for co-incubation of both drugs for the entire +96–120 hour period. The entire approach attempted to simulate in vivo co-exposure to safingol for only a portion of the entire HPR treatment period.

Figure 10:
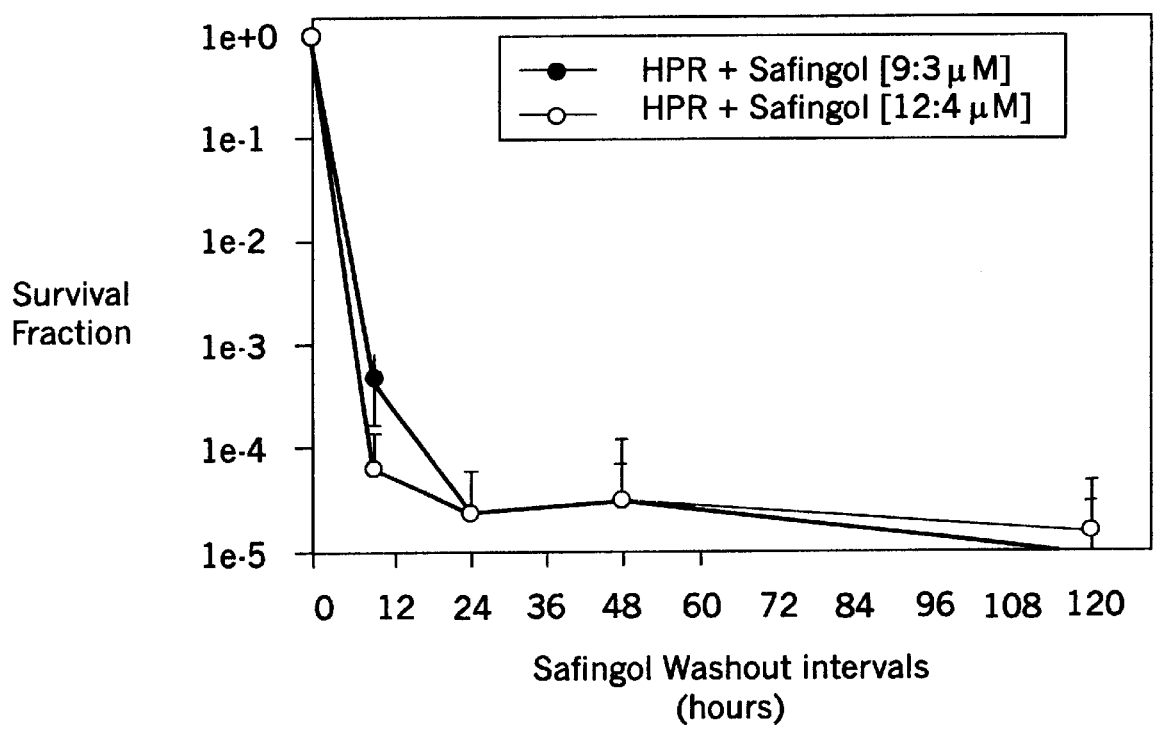
FIG. 10 illustrates CHLA-90 cells treated with HPR (fenretinide) and safingol, with the safingol washed out at various time intervals and replaced by pre-equilibrated, HPR-only medium at the time indicated.
Figure 11:
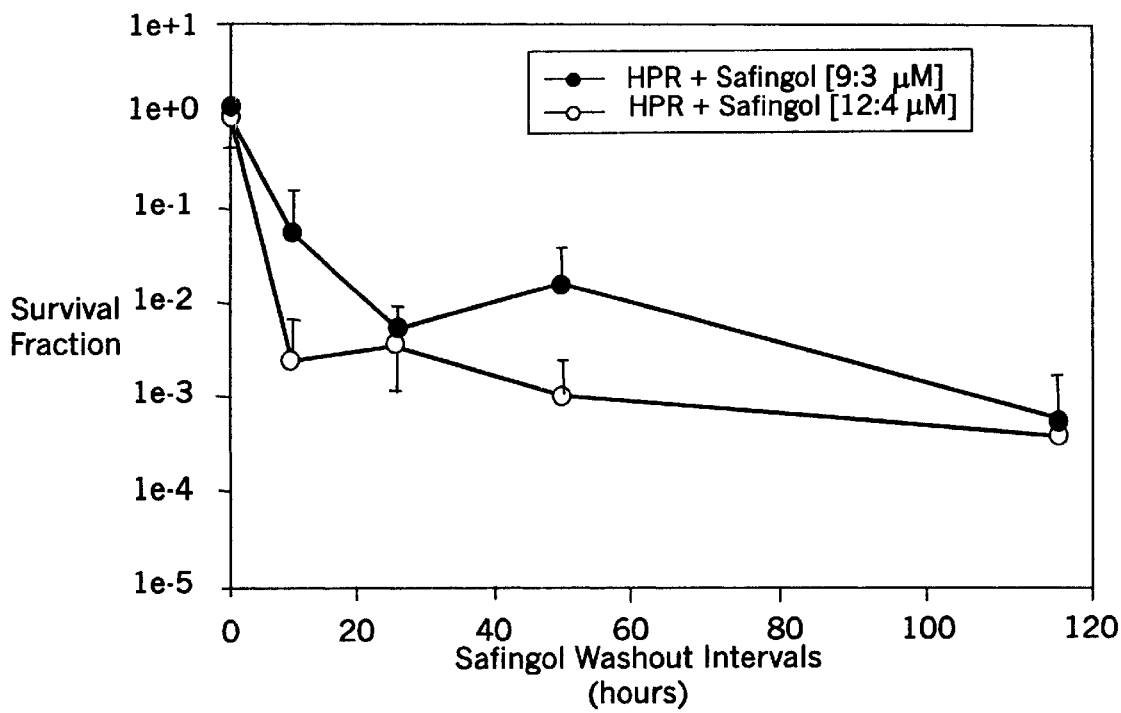
FIG. 11 illustrates sk-N-RA cells treated with HPR and safingol, with the safingol washed out at various time intervals and replaced by pre-equilibrated, HPR-only medium at the time indicated.
Figure 12:
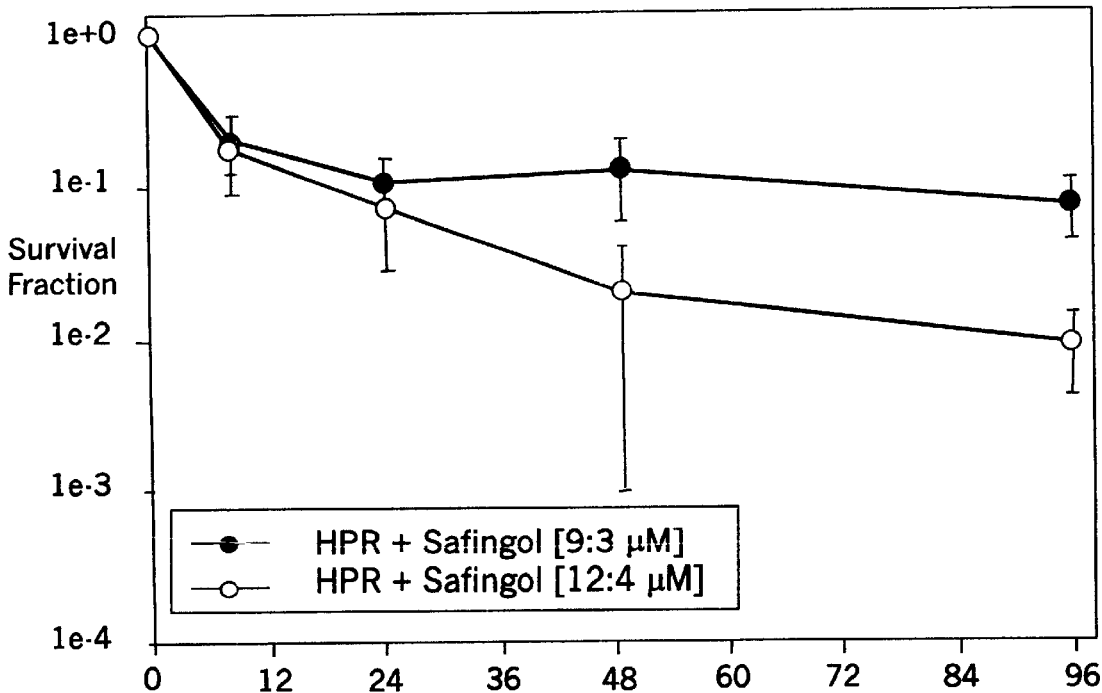
FIG. 12 illustrates A549 lung cancer cells treated with HPR and safingol, with the safingol washed out at various time intervals and replaced by pre-equilibrated, HPR-only medium at the time indicated.

Results. FIGS. 10, 11 and 12 are representative cytotoxicity results obtained in various cell lines when safingol is co-present with HPR for less than the entire HPR treatment period. A large portion of the increase in tumor cell kill caused by the invention can be obtained, in some instances, by co-presence of tile drugs for less than the entire HPR treatment period. In some instances, co-exposure of safingol and HPR for only a small fraction of the entire HPR-treatment period is sufficient for the invention to function. This demonstrates that all compounds need not be present at all times for the invention to function.

EXAMPLE 11

The Cytotoxicity of Other Retinoids is Increased by Safingol

The retinoid, all-trans-retinoic acid (ATRA), has been previously shown to cause modest (1.5×) increases in the level of ceramide of Neuro2a neuroblastoma cells (L. Riboni et al., *J. Biol. Chem.* 270; 26868 (1995)). Here we demonstrate that the co-exposure of ATRA, or the retinoid, 13-cis-retinoic acid, with safingol results in significantly decreased cell survival in CHLA-90 and LAN-6 neuroblastoma cells compared to that of either retinoid alone. This demonstrates that the invention is active with various different retinoids.

Methods. Cells were added in 100 μL whole medium per well to 96-well microplates for DIMSCAN cytotoxicity assay as previously described. Cell lines used were the neuroblastoma cell lines CHLA-90 and LAN-6. At Time=0, either all-trans-retinoic acid (ATRA), 13-cis-retinoic acid (13-cis-RA) or a combination of retinoid plus safingol at a 3:1 molar ratio were added in 50 μL whole medium. Plates were incubated and assayed for cytotoxicity by DIMSCAN assay at +120 for CHLA-90 cells and+144 hours for LAN-6 cells.

Figure 13:
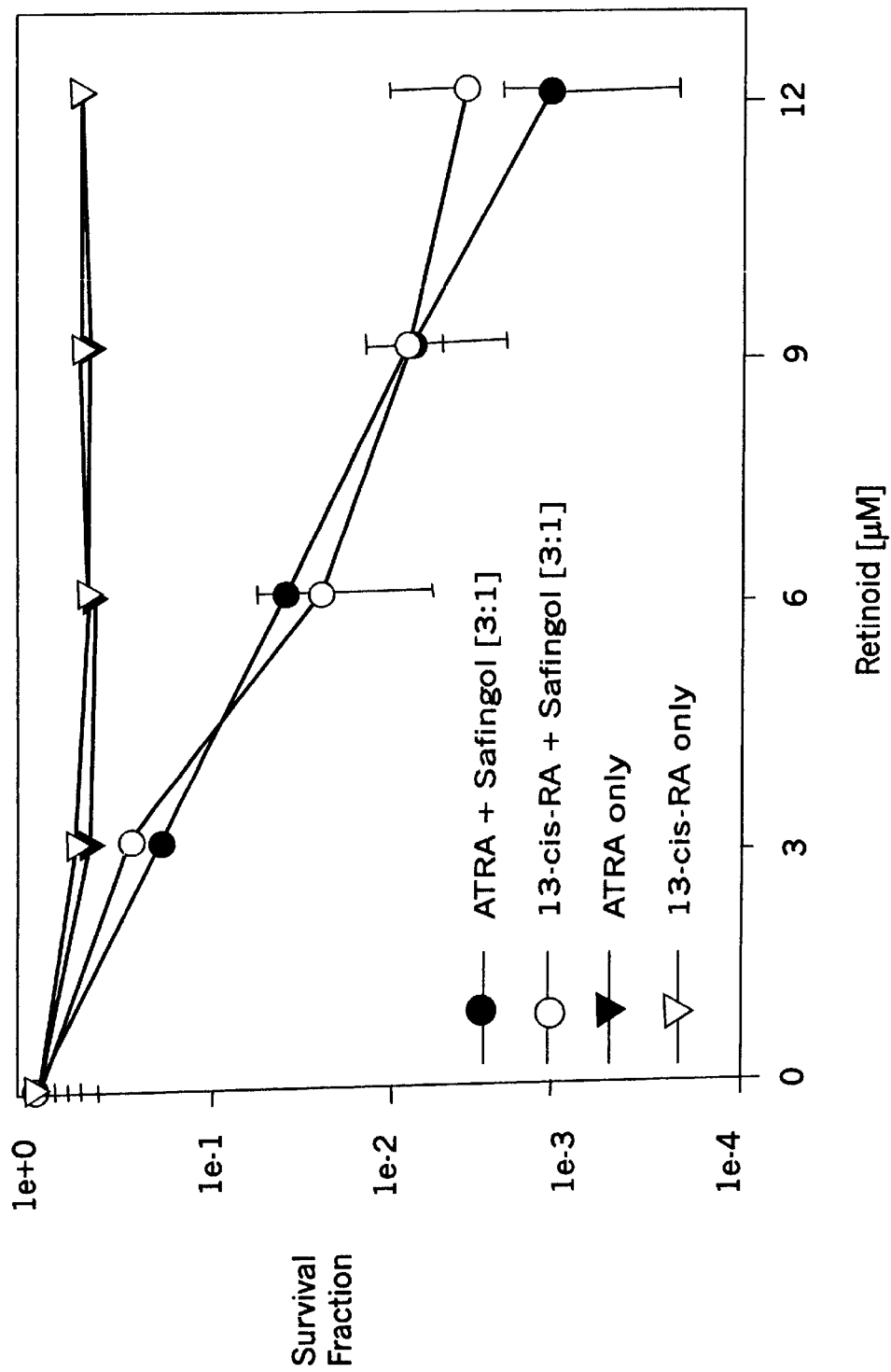
FIG. 13 illustrates CHLA-90 cells treated with safingol and all trans-retinoic acid (ATRA), or safingol and 13-cis-retinoic acid.
Figure 14:
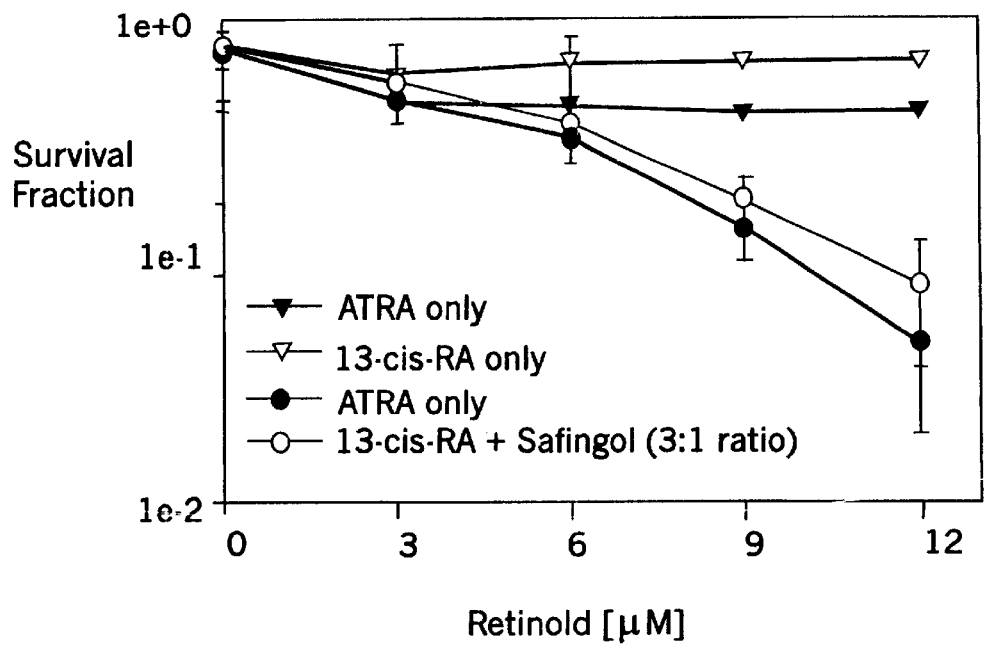
FIG. 14 illustrates LAN-6 cells treated with safingol and all trans-retinoic acid (ATRA), or safingol and 1 3-cis-retinoic acid.

Results. The data set forth in FIGS. 13–14 demonstrate that the addition of safingol to the retinoids ATRA or 13-cis-RA causes a significant decrease in the cell survival of the CHLA-90 and LAN-6 cell lines. Safingol at 4 μM (the maximum concentration used in the experiments below) had a Survival Fraction of 0.11 in CHLA-90 and of 0.39 in LAN-6 cells. This demonstrates that the invention is active with a number of different retinoids.

EXAMPLE 12

Specific Conversion of Ceramide into Nontoxic Glucosyl-ceramide Decreases the Cytotoxicity of HPR and HPR+Safingol We have shown that HPR generates ceramide in neuroblastoma tumor cell lines in a dose- and time-depenent manner (B. Maurer et al., *J. Natl. Cancer Inst.* (1999)(in press)). Glucosylceramide (GC) is a nontoxic metabolite of ceramide. Ceramide is converted into glucosylceramide by the action of glucosylceramide synthase (GCS). Glucosylceramide synthase (GCS) has been transfected into human MCF7 breast cancer cells in a tetracycline-inducible expression construct in the MCF7/GCS cell line (Y. Liu et al., *J. Biol. Chem.* 274:1140–46 (1999)). Incubation of MCF7/ GCS cells in doxycycline (a tetracycline)-containing medium has been shown to increase GCS activity, increase the conversion of ceramide into glucosylceramide, and to decrease the cytotoxicity of Adriamycin, a drug known to increase ceramide in these cells (Y. Liu et al., supra). We have exposed MCF7/GCS cells to HPR, safingol and HPR+ safingol in the absence, and in the presence, of doxycycline. We have found that increasing the activity of GCS with doxycycline in MCF7/GCS cells significantly decreases HPR cytotoxicity and significantly decreases the cytotoxicity of the HPR+safingol drug combination. This demonstrates that the ceramide generated by HPR in MCF7/GCS cells is cytoxic and that the Invention is at least partially dependent upon ceramide and the enhancement of its cytotoxicity.

Methods. MCF7/GCS cells were plated and incubated in RPMI medium with 10% fetal bovine serum and 200 microgram/ml Hygromycin B (tet OFF) for DIMSCAN cytotoxicity assays as previously described. To increase GCS expression, MCF7/GCS cells were also incubated in the above medium with 3 microgram/ml doxycycline (tet ON) for three days prior to replating them for DIMSCAN cytotoxicity assay. DIMSCAN assays with doxycycline-induced (tet ON) cells also included 3 microgram/ml doxycycline in the medium. Both "tet OFF" and "tet ON" MCF7/GCS cells were exposed to HPR, safingol and HPR+safingol (3:1 molar ratio) for 96 hours and assayed for survival fraction by DIMSCAN as previously described.

Figure 15:
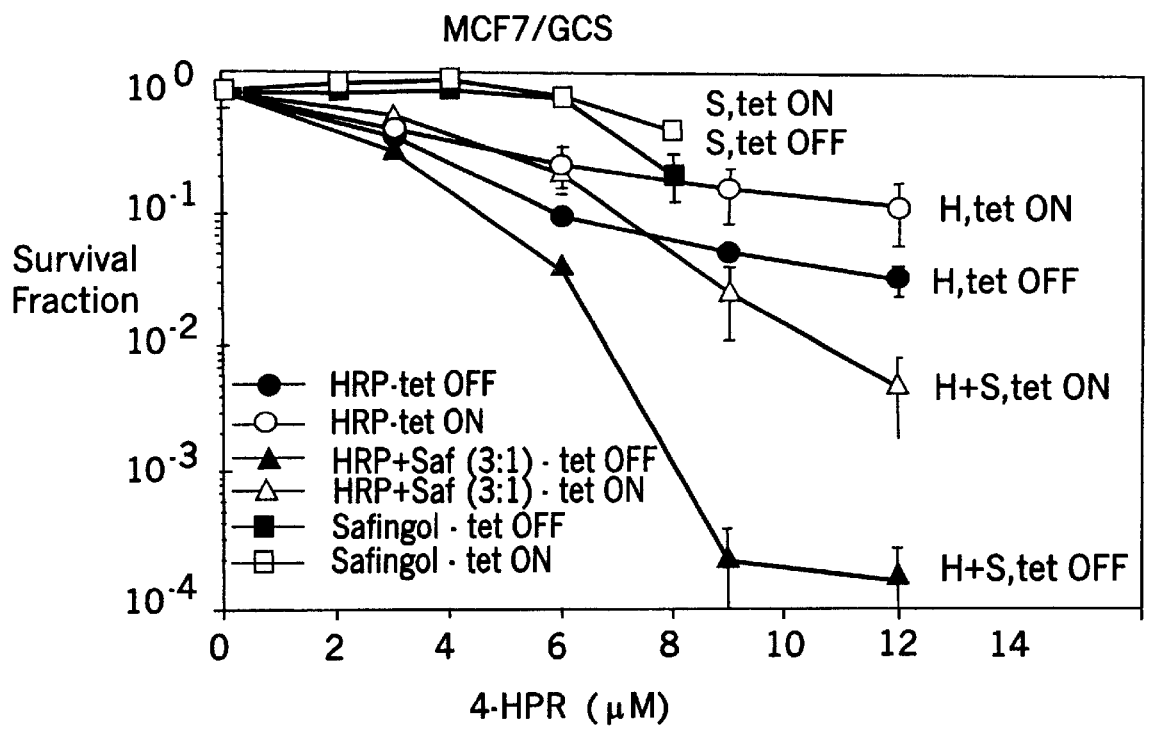
FIG. 15 illustrates that the conversion of ceramide into nontoxic glucosyl1-ceramide decreases the cytotoxicity of HPR and HPR+safingol. Note the HPR+safingol is a 3:1 molar ratio (e.g.: 9 $\mu$M HPR +3 $\mu$M safingol).

Results. Representative results are shown in FIG. 15. Co-incubation of MCF7/GCS cells with doxycycline ("tet ON"), previously shown to increase GCS expression and to increase the conversion of ceramide to nontoxic glucosylceramide (Y. Liu et al., supra), significantly decreased (P<0.005 by student's t-test at >6 $\mu$M HPR) the cytotoxicity of HPR and HPR+safingol compared to "tet OFF" MCF7/GCS cells. There was no significant decrease in the cytotoxicity of safingol in the range of concentrations (0–4 $\mu$M) used in the HPR+safingol combination studies. This demonstrates that HPR cytotoxicity is partially dependent upon the generation of cytotoxic ceramide. It farther demonstrates that the activity of the HPR+safingol drug combination (part of the Invention) is also at least partially dependent upon the generation of cytotoxic ceramide and enhancement of its cytotoxicity.

EXAMPLE 13

HPR and HPR+Safingol Induce Cell Death by a Combination of Apoptosis and Necrosis; HPR and HPR+Safingol Can Induce Cell Death by Necrosis if Apoptotic Cell Death is Inhibited There are two main mechanisms currently recognized that lead to cell death after biochemical cellular insult, apoptosis and necrosis (G. Nunez G. et al., Oncogene 17:323745 (1998); G. Cohen, Biochem. J. 326:1–16 (1997); Y. Hannun, Blood 89:1845–53 (1997); N. Thornberry, Chem. Biol. 5: R97–103 (1998); N. Zamzami et al., J. Bioenerg Biomembr. 29:185–193 (1997); D. McConkey, Toxicol. Lett. 99:157–98 (1998); M. Raffray and G. Cohen, Pharmacol Ther. 75:153–77 (1997); J. Lemasters, Am. J. Physiol. 276:G1–6 (1999)). Apoptosis consists of a series of fairly specific, fairly sequential, enzymatic activation steps (the caspase enzyme cascade) which usually lead to a specific type of DNA degradation (internucleosomal DNA laddering) and cell death. Apoptosis is typified morphologically by condensed nuclear chromatin and fragmentation of the nuclei into apoptotic bodies in cells which have not lost membrane integrity and an increase in sub $G_0/G_1$ DNA content by flow cytometry. Necrosis is a less biochemically-defined condition that is characterized by a general breakdown in cell membrane integrity and associated with decreased levels of intracellular of ATP (C. Renvoize et al., Cell Biol. Toxicol 14:111–20 (1998).). Necrosis is typified morphologically by a loss of membrane integrity (demonstrated by propidium iodide staining) with cell rounding and cell detachment. These two processes may overlap in parts of their biochemical mechanism, but are generally considered distinct or, at least, at opposite ends of a mechanistic continuum. As shown below, both HPR and HPR+safingol cause cell death through a combination of both apoptosis and necrosis. These observations are significant because tumor cells with impaired apoptotic mechanisms may be killed by necrosis. Thus, the drug combinations described herein have a significant advantage (induction of cell death by necrosis, as well as by apoptosis) over other methods of antitumor killing which rely primarily on an intact apoptotic mechanisms or upon enhancement of apoptosis.

Methods. To determine the manner in which 4-HPR or HPR+safingol induced cell death in neuroblastoma cells, morphological evidence of apoptosis and/or necrosis was assessed in CHLA-90 cells in the presence or absence of a specific as inhibitor of apoptosis, the neural cell-penetrant, pan-caspase enzyme inhibitor, BOC-d-fink (Enzyme Systems Products, Livermore, Calif.). BOC-d-fmk specifically inhibits, and prevents death by, the caspase enzymes that mediate apoptosis. CHLA-90 cells were plated in duplicate in whole medium in Lab Tek chamber slides (Nunc, Naperville, Ill.), allowed to attach for 24 hours, and then treated in the presence or absence of BOC-d-fink (40 $\mu$M) for one hour prior to treatment with HPR (10 $\mu$M). Control cells were treated with vehicle solvents of 0. 1% ethanol (4-HPR) and/or 0.2% DMSO (BOC-d-fink). Morphological features of apoptosis (DNA condensation and/or apoptotic bodies) were visualized in undetached cells at +24 or +48 hours using blue nuclear fluorescence induced by the supravital DNA stain Hoechst 33342 (10 $\mu$g/ml for 30 mins at 37° C.), while necrotic cells and advanced apoptotic cells were recognized by red fluorescent staining with propidium iodide (0.5 $\mu$M/ml). Red fluorescently-staining cells with condensed nuclear remnants were scored as apoptotic cells. For cells assayed at +48 hours, additional BOC-d-fink (40 $\mu$M) or appropriate control vehicle was added at +24 hours. Cells were observed using filters appropriate for each dye sequentially on an Olympus Vanox epifluorescence microscope. Mutiple random fields of cells (of ~100–500 cells each) were counted and photographed for viable cells, apoptotic cells, and necrotic cells. To further examine cells treated with HPR, cytotoxicity assays were performed on CHLA-90 cells pretreated with or without 40 $\mu$M BOC-d-fmk for one hour prior to the addition of 4-HPR (3–10 $\mu$M) and assayed at +24 hours by DIMSCAN assay to assess the effect of caspase inhibition on viability. Control cells were treated with vehicle solvents of 0.1% ethanol (4-HPR) and/or 0.2% DMSO (BOC-d-fink). Assessment of apoptosis by flow cytometry (Z. Darnzynkiewicz et al., Cytometry 13:795–808 (1992)) used propidium iodide in a hypotonic lysis buffer (A. Krishan et al., J. Cell Biology, 66:188–193 (1975)), to identify cells with a sub $G_0/G_1$ DNA content. Cells were treated as above and assayed at +24 hours. The stained nuclei were analyzed on a Coulter Epics ELITE flow cytometer with a 488 nm Argon laser and a 20 nm band pass filter centered on 610 nm. Error bars indicate 95% Confidence Intervals. Statistical analysis was by unpaired, two-sided Student's t-test. All P-values are two-sided.

Figure 16:
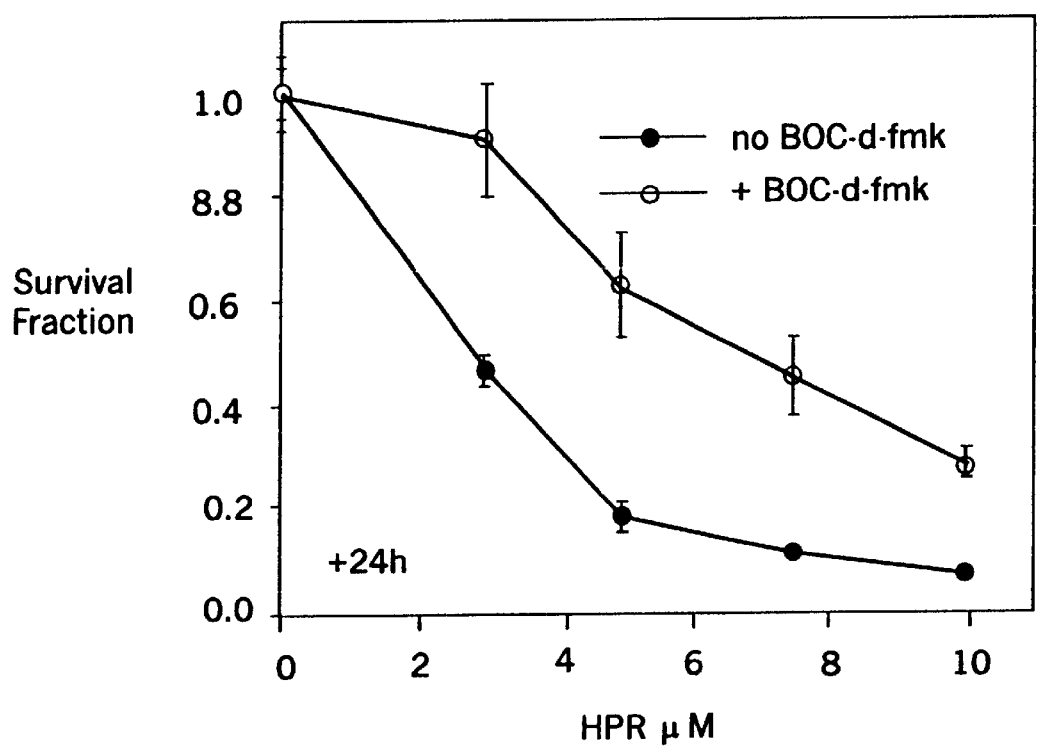
FIG. 16 shows that the cytotoxicity of HPR was significantly reduced by the pan-caspace enzyme BOC-d

Results. As shown in FIG. 16, the cytotoxicity of HPR was significantly reduced by the pan-caspase enzyme, apoptosis-inhibitor, BOC-d-fmk (40 $\mu$M), across all HPR concentrations (P<0.001), but HPR still induced significant cytotoxicity in the presence of BOC-d-fmk (at 3 $\mu$M HPR, P=0.002, at >3 $\mu$M HPR, P<0.001). These results indicate that HPR kills cells by both apoptotic and nonapoptotic (necrotic) mechanisms.

Figure 17:
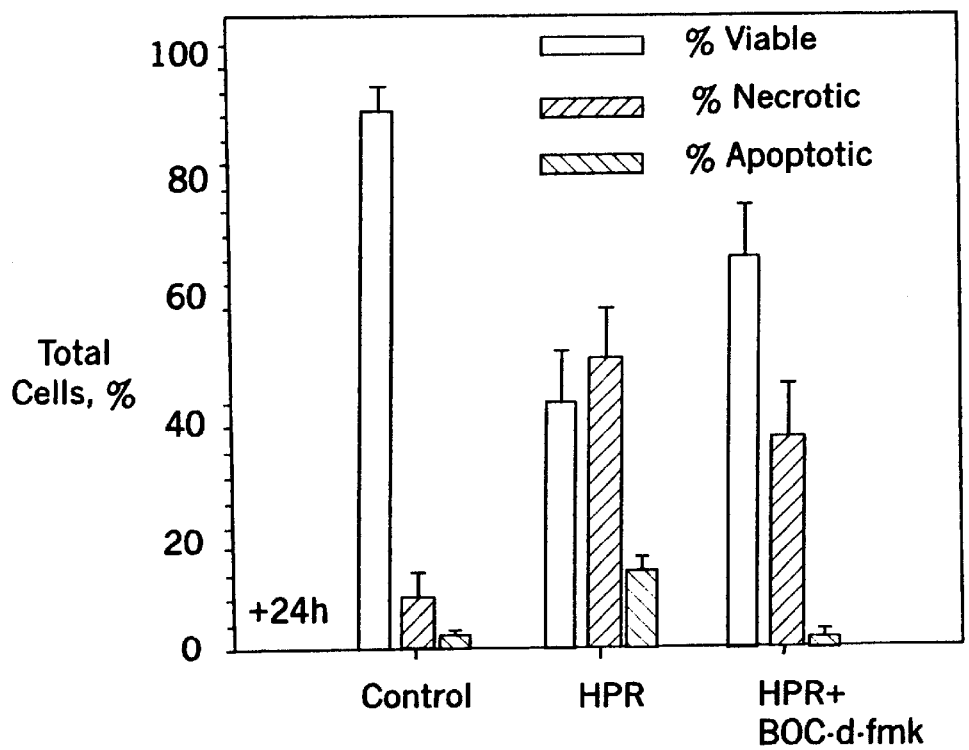
FIG. 17 shows that pretreatment with BOC-d-fmk prior to HPR exposure significantly reduced morphological nuclear changes indicative of apoptosis.

FIG. 17. Pretreatment with BOC-d-fink prior to HPR exposure significantly reduced (P=0.001) the morphological nuclear changes indicative of apoptosis (condensed, intensely-staining nuclear chromatin and fragmentation of the nuclei into apoptotic bodies which have not lost membrane activity) in CHLA-90 cells. However, the significant morphological evidence of necrosis (P=0.002) induced by HPR (loss of membrane integrity demonstrated by propidium iodide staining and cell rounding) was minimally affected by BOC-d-fink and was still significant (P=0.016) relative to controls. HPR alone induced significant apoptosis (P=0.006), while apoptosis in cells treated with HPR+BOC-d-fink was not significantly different from controls (P=0.48). These results indicate that HPR-induced cell death proceeds by mixed apoptosis/necrosis and can proceed by necrotic mechanisms even if death by apoptosis is inhibited.

FIG. 18. At +24 hours, BOC-d-fmk (40 $\mu$M) abrogated the sub $G_0/G_1$ DNA-fragmentation induced by HPR (10 $\mu$M) in CHLA-90 as detected by flow cytometry that is a characteristic of apoptosis. As a significant fraction of CHLA-90 cells were dead or dying at +24 hours, this data provides evidence that HPR can kill cells by nonapoptotic (necrotic) mechanisms.

Cell death induced by HPR (10–20 $\mu$M) has also recently been reported to proceed by necrosis in lymphoblastoid cell lines (L. Spreinger and B. Stewart, *Cancer Lett.* 128:189–196 (1998)) and in an embryonal carcinoma cell line (J. Clifford et al., *Cancer Res.* 59:14–18 (1999).).

Figure 19:
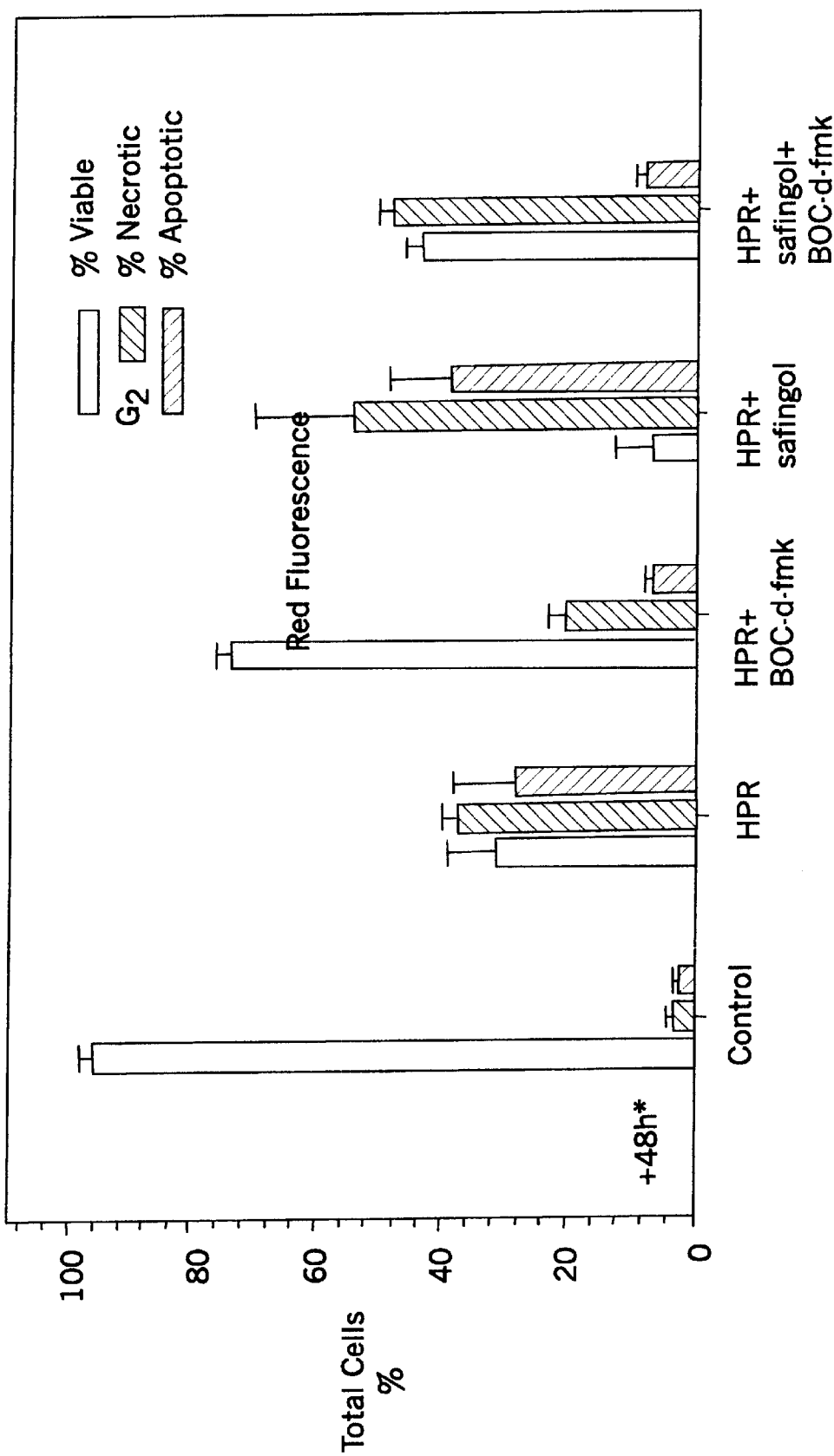
FIG. 19 shows that pretreatment with BOC-d-fmk prior to HPR or HPR+safingol exposure reduced by morphological changes indicative of apoptosis, but that the morphological evidence of necrosis induced by the HPR+safingol combination was minimally affected by BOC-d-fmk.

FIG. 19. Pretreatment with BOC-d-fmk prior to HPR or HPR+safingol (10:3 micromolar ratio) exposure reduced the morphological nuclear changes indicative of apoptosis in CHLA-90 cells at +48 hours. However, the morphological evidence of necrosis induced by the HPR+safingol drug combination at +48 hours was minimally affected by BOC-d-fmk and was still significant ( P<0.001) relative to controls. These results indicate that the drug combination HPR+safingol (an embodiment of the invention) can induce cell death by mixed apoptosis/necrosis and that cell death can proceed by necrotic mechanisms even if death by apoptosis is inhibited.

EXAMPLE 14

Safingol Synergizes 4-HPR Cytotoxicity in Multiple Tumor Cell Lines

As reported above, we have succeeded in increasing the cytotoxicity of 4-HPR through inhibition of several ceramide-related pathways. Most of the inhibitors used have been only studied in vitro. However, safingol, a PKC inhibitor with activity against ceramide-activated PKC-$\zeta$, recently received a partial Phase I evaluation (G. Schwartz et al., *Clin. Cancer Res.* 3, 537–543 (1997)). This trial was terminated prematurely do to lack of drug. However, Phase I results showed that a one hour infusion of safingol at 120 mg/m$^2$ achieved 3 $\mu$M serum levels during infusion, with no reported toxicities. Therefore, we undertook cytoxicity studies of 4-HPR +safingol at a fixed 3:1 molar ratio of HPR:safingol at concentrations expected to be achieved in humans from these results and animal model data (G. Kelloff et al., *J. Cell. Biochem. Suppl.* 20, 176–196 (1994); L. Kedderis et al., *Fund. Appl. Tox.* 25, 201 (1995)). The activity of 4-HPR +safingol was first tested in a model panel of neuroblastoma cells which included several highly alkylator-resistant cell lines. We then tested 4-HPR +safingol in cell lines derived from other tumor types. These results are summarized in Table 1, which also shows the Combination Index (CI) calculated by Chou analysis as a measure of drug synergy (CI is a term to describe the pharmacologic effect of two drugs in combination. A CI<1 indicates synergy, with smaller numbers indicating greater synergy; a CI equal to 1 signifies additive effect; and a CI>1 means the drug combination is antagonistic). It is notable that multi-log cytotoxicity was achieved in cell lines that were p53 null or mutant and in cell lines that are highly resistant to alkylating agents. Our results demonstrate that safingol significantly enhances and even synergizes the cytotoxicity of 4-HPR against tumor cell lines of multiple tumor types in a p53-independent fashion.

TABLE 1

Combination Index of HPR + Safingol (3:1) from 0–12 $\mu$M HPR

| Cell Type | | Combination Index (CI) ED99 | Log Cell Kill HPR (3:1) 9 $\mu$M | 12 $\mu$M |
|---|---|---|---|---|
| Neuroblastoma | | | | |
| SK-N-RA | | <0.1 | 1.9 | 3 |
| SMS-LHN | Pd-IND | <0.1 | 3.5 | |
| CHLA-90 | Pd-BMT | <0.1 | 3.1 | 4 |
| CHLA-171 | | <0.1 | 2.9 | 4 |
| CHLA-79 | Pd-BMT | <0.1 | 3.5 | 4 |
| Lung | | | | |
| NCI-H146 SCLC | >c-myc | <0.1 | 3.2 | 4 |
| NCI-H157 squamous | | <0.1 | 2.9 | 4 |
| NCI-H1792 | | <0.1 | 2.1 | 4 |
| A549 | p53 wt | 0.2 | 1 | 2 |
| Melanoma | | | | |
| A 375 | p53 wt | <0.1 | 2.6 | 4 |
| A2058 | | 0.2 | 0.9 | 2.7 |
| Prostate | | | | |
| LNCaP.FGC | p53 wt | <0.1 | 2.8 | 4 |
| PC-3 | p53 null | 1.0 | 1.4 | 1.9 |
| Colon | | | | |
| LoVo | p53 wt | 0.1 | 0.5 | 1.8 |
| HT-29 | p53 mut | 0.3 | 1.3 | 2.4 |
| Breast | | | | |
| MCF7 | p53 wt | 0.5 | 1.1 | 1.5 |
| DoxR MCF7 | | 0.1 | 0.9 | 1.5 |
| MDA-MB-231 | p53 mut | 0.3 | 0.9 | 3 |
| Pancreas | | | | |
| PANC-1 epitheliod | p53 mut | 0.2 | 0.3 | 1.7 |
| Hs 766T | | 1.7 | 2.9 | 2.5 |

| Combination Index (CI) | Description |
|---|---|
| <0.1 | very strong synergism |
| 0.1–0.3 | strong synergism |
| 0.3–0.7 | synergism |
| 0.7–0.85 | moderate synergism |
| 0.85–0.9 | slight synergism |
| 0.9–1.10 | nearly additive |
| 1.1–1.20 | slight antagonism |

EXAMPLE 15

Inhibitors of 1-O-acylceramide Transferase Increase Fenretinide (4-HPR) Cytotoxicity. Inhibitors That Inhibit Both Glucosylceramide Synthase (GCS) and 1-O-acylceramide Transferase Increase 4-HPR Cytoxicity Here we show, using stereoisomers of the more potent PPMP, that inhibitors of 1-O-acylceramide synthase, such as D,L-erythro-PPMP significantly increase the cytotoxicity of HPR in two neuroblastoma cell lines, and hence, are active and claimed in the invention. Furthermore, we show that compounds that inhibit both GCS and 1-O-acylceramide synthase, such as D,L-threo-PPMP significantly increase the cytotoxicity of 4-HPR.

Methods. The neuroblastoma cell lines, CHLA-90 and SK-N-RA, were added in 100 μL of whole medium per well to 96-well microplates for DIMSCAN cytotoxicity assays as previously described. At time=+0, HPR; D,L-threo- or D,L-erythro-PPMP; or HPR plus D,L-threo- or D,L-erythro-PPMP (at a 1:1 micromolar ratio); were added to the final drug concentrations listed, in 50 μL of whole medium per well (a final total of 150 μL medium per well). Plates were incubated at 37° C. and $C_i$: assayed for cytotoxicity by DIMSCAN assay at +96–120 hours. Cytotoxocity is expressed as the fraction of cells surviving (Survival Fraction, S.F.). Error bars represent 95% Confidence Intervals. Cytotoxic synergy was analyzed by Combination Index (C.I.) analysis calculated at the dose lethal to 99% of exposed cells (LD99). Statistical analysis of the differences in mean cytotoxicity was evaluated by the unpaired, two-sided Student's t test.

Figure 20:
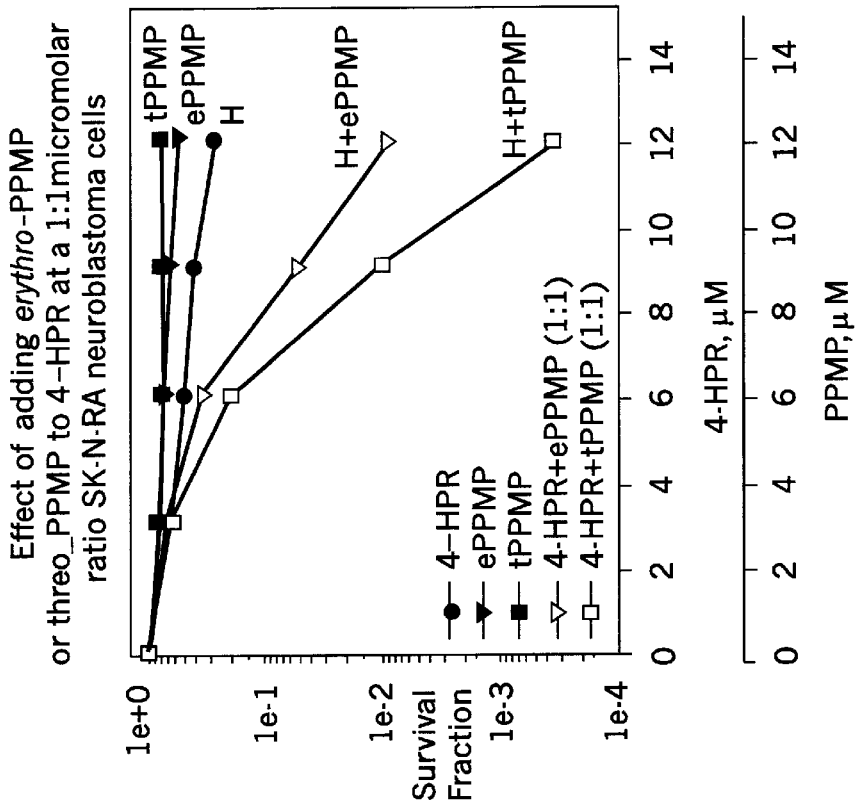
FIG. 20 shows the effect of adding erythro-PPMP or threo-PPMP to 4-HPR at a 1:1 micromolar ratio in CHLA-90 neuroblastoma cells.
Figure 21:
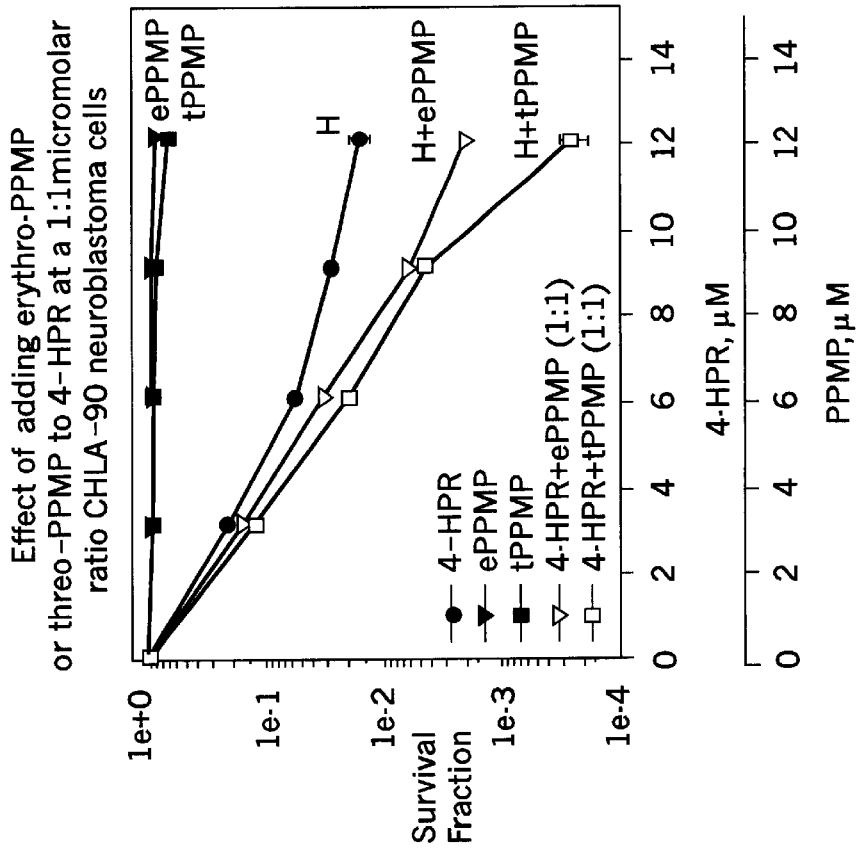
FIG. 21 shows the effect of adding erythro-PPMP or threo-PPMP to 4-HPR at a 1:1 micromolar ratio in SK-N-RA neuroblastoma cells.

Results. The representative data (shown in FIG. 20 and FIG. 21) demonstrate that the 1-O-acylceramide synthase inhibitor D,L-erythro-PPMP significant increases HPR cytotoxicity in the CHLA-90 (C.I.=0.18, strong synergism) and SK-N-RA (C.I.<0.06, very strong synergism) cell lines. The data also demonstrate that D,L-threo-PPMP, which inhibits both 1-O-acylceramide synthase and GCS, at equimolar concentrations causes an even greater increase in HPR cytotoxicity than D,L-erythro-PPMP in both cell lines (in CHLA-90: C.I.<0.09, very strong synergism; threo-PPMP cytotoxicity greater than eythro-PPMP cytotoxicity at 3–12 μM (P<0.001); in SK-N-RA: C.I.<0.01, very strong synergism; threo-PPMP cytotoxicity greater than eythro-PPMP cytotoxicity 6–12 μM (P<0.001)).

Significance. The results show that inhibitors that simultaneously inhibit 1-O-acylceramide transferase and glucosylceramide synthase, such as D,L-threo-PPMP, increase the cytotoxicity of HPR, have been previously shown to increase the cytotoxocity of HPR+plus safingol, in accordance with the instant the Invention. The results show that inhibitors of 1-O-acylceramide transferase, such as D,L-erythro-PPMP, increase the cytotoxicity of HPR, increase the cytotoxicity of HPR plus safingol.

The foregoing is illustrative of the present invention, and is not to be construed as limiting thereof. The invention is defined by the following claims, with equivalents of the claims to be included therein.

We claim:

1. A method of treating a hyperproliferative disorder in a subject in need of treatment, comprising administering to said subject, in combination, a hyperproliferative disorder treatment effective amount of:
   (a) a ceramide-generating retinoid comprising a retinoic acid derivative or a pharmaceutically acceptable salt thereof; and
   (b) a ceramide degradation inhibitor or a pharmaceutically acceptable salt thereof;
   wherein said hyperproliferative disorder is a cancer selected from the group consisting of leukemia, neuroblastoma, lung cancer, skin cancer, prostate cancer, colon cancer, breast cancer, and pancreatic cancer;
   and wherein the retinoic acid derivative is given in an amount effective to produce necrosis, apoptosis, or both in the cancer, and the ceramide degradation inhibitor is given in an amount effective to increase the necrosis, apoptosis or both produced in the cancer over that expected to be produced by the sum of that produced by the retinoic acid derivative and the ceramide degradation inhibitor when given separately.

2. A method according to claim 1, wherein said ceramide degradation inhibitor is selected from the group consisting of glucosyl ceramide synthase inhibitors, 1-acylceramide synthesis inhibitors, sphingosine-1-phosphate synthesis inhibitors, protein kinase C inhibitors, and the pharmaceutically acceptable salts thereof.

3. A method of treating a hyperproliferative disorder in a subject in need of such treatment, comprising administering to said subject, in combination, a hyperproliferative disorder treatment effective amount of:
   (a) a ceramide-generating retinoid comprising a retinoic acid derivative or a pharmaceutically acceptable salt thereof; and
   (b) a glucosylceramide synthesis inhibitor or a pharmaceutically acceptable salt thereof;
   wherein said hyperproliferative disorder is a cancer selected from the group consisting of leukemia, neuroblastoma, lung cancer, skin cancer, prostate cancer, colon cancer, breast cancer, and pancreatic cancer;
   and wherein the retinoic acid derivative is given in an amount effective to produce necrosis, apoptosis, or both in the cancer, and the glucosylceramide synthesis inhibitor is given in an amount effective to increase the necrosis, apoptosis or both produced in the cancer over that expected to be produced by the sum of that produced by the retinoic acid derivative and the glucosylceramide synthesis inhibitor when given separately.

4. A method according to claim 3, wherein said ceramide-generating retinoid is fenretinide or a pharmaceutically acceptable salt thereof.

5. A method according to claim 3, wherein said glucosyl ceramide synthesis inhibitor is 1-phenyl-2-palmitoylamino-3-morpholino-1-propanol or a pharmaceutically acceptable salt thereof.

6. A method of treating a hyperproliferative disorder in a subject in need of such treatment, comprising administering to said subject, in combination, a hyperproliferative disorder treatment effective amount of:
   (a) a ceramide generating retinoid comprising a retinoic acid derivative or a pharmaceutically acceptable salt thereof; and
   (b) a sphingosine-1-phosphate synthesis inhibitor or a pharmaceutically acceptable salt thereof;
   wherein said hyperproliferative disorder is a cancer selected from the group consisting of leukemia, neuroblastoma, lung cancer, skin cancer, prostate cancer, colon cancer, breast cancer, and pancreatic cancer;
   and wherein the retinoic acid derivative is given in an amount effective to produce necrosis, apoptosis, or both in the cancer, and the sphingosine-1-phosphate synthesis inhibitor is given in an amount effective to increase the necrosis, apoptosis or both produced in the cancer over that expected to be produced by the sum of that produced by the retinoic acid derivative and the sphingosine-1-phosphate synthesis inhibitor when given separately.

7. A method according to claim 6, wherein said ceramide-generating retinoid is fenretinide or a pharmaceutically acceptable salt thereof.

8. A method according to claim 6, wherein said sphingosine-1-phosphate synthesis inhibitor is a sphingosine kinase inhibitor or a pharmaceutically acceptable salt thereof.

9. A method according to claim 6, wherein said sphingosine-1-phosphate synthesis inhibitor is D-erythro-N,N-dimethylsphingosine or a pharmaceutically acceptable salt thereof.

10. A method of treating a hyperproliferative disorder in a subject in need of such treatment, comprising administering to said subject, in combination, a hyperproliferative disorder treatment effective amount of:
   (a) a ceramide-generating retinoid comprising a retinoic acid derivative or a pharmaceutically acceptable salt thereof; and
   (b) a protein kinase C inhibitor or a pharmaceutically acceptable salt thereof;
   wherein said hyperproliferative disorder is a cancer selected from the group consisting of leukemia, neuroblastoma, lung cancer, skin cancer, prostate cancer, colon cancer, breast cancer, and pancreatic cancer;
   and wherein the retinoic acid derivative is given in an amount effective to produce necrosis, apoptosis, or both in the cancer, and the protein kinase C inhibitor is given in an amount effective to increase the necrosis, apoptosis or both produced in the cancer over that expected to be produced by the sum of that produced by the retinoic acid derivative and the protein kinase C inhibitor when given separately.

11. A method according to claim 10, wherein said ceramide-generating retinoid is fenretinide or a pharmaceutically acceptable salt thereof.

12. A method according to claim 10, wherein said protein kinase C inhibitor is L-threo-dihydrosphingosine or a pharmaceutically acceptable salt thereof.

13. A method of treating a hyperproliferative disorder in a subject in need of such treatment, comprising administering to said subject, in combination, a hyperproliferative disorder treatment effective amount of:
   (a) a ceramide-generating retinoid comprising a retinoic acid derivative or a pharmaceutically acceptable salt thereof; and
   (b) at least two compounds selected from the group consisting of (i) glucosylceramide synthesis inhibitors and the pharmaceutically acceptable salts thereof, (ii) sphingosine-1-phosphate synthesis inhibitors and the pharmaceutically acceptable salts thereof, and (iii) protein kinase C inhibitors and the pharmaceutically acceptable salts thereof;
   wherein said hyperproliferative disorder is a cancer selected from the group consisting of leukemia, neuroblastoma, lung cancer, skin cancer, prostate cancer, colon cancer, breast cancer, and pancreatic cancer;
   and wherein the retinoic acid derivative is given in an amount effective to produce necrosis, apoptosis, or both in the cancer, and the at least two compounds are given in an amount effective to increase the necrosis, apoptosis or both produced in the cancer over that expected to be produced by the sum of that produced by the retinoic acid derivative and the at least two compounds when given separately.

14. A method according to claim 13, wherein said ceramide generating retinoid is fenretinide or a pharmaceutically acceptable salt thereof.

15. A method according to claim 13, wherein said at least two compounds comprise (i) a glucosylceramide synthesis inhibitor or a pharmaceutically acceptable salt thereof and (ii) either a sphingosine-1-phosphate synthesis inhibitor, a protein kinase C inhibitor, or a pharmaceutically acceptable salt thereof.

16. A method according to claim 13, wherein said at least two compounds comprise a glucosylceramide synthesis inhibitor or a pharmaceutically acceptable salt thereof, and a sphingosine-1-phosphate synthesis inhibitor or a pharmaceutically acceptable salt thereof.

17. A method according to claim 13, wherein said at least two compounds comprise a glucosylceramide synthesis inhibitor or a pharmaceutically acceptable salt thereof, and a protein kinase C inhibitor or a pharmaceutically acceptable salt thereof.

18. A method according to claim 13, wherein said at least two compounds comprise a sphingosine-1-phosphate synthesis inhibitor or a pharmaceutically acceptable salt thereof, and a protein kinase C inhibitor or a pharmaceutically acceptable salt thereof.

19. A method according to claim 13, wherein said at least two compounds comprise a glucosylceramide synthesis inhibitor or a pharmaceutically acceptable salt thereof, a sphingosine-1-phosphate synthesis inhibitor or a pharmaceutically acceptable salt thereof, and a protein kinase C inhibitor or a pharmaceutically acceptable salt thereof.

20. A method of treating a hyperproliferative disorder in a subject in need of such treatment, comprising administering to said subject, in combination, a hyperproliferative disorder treatment effective amount of:
   (a) a ceramide-generating retinoid comprising a retinoic acid derivative or a pharmaceutically acceptable salt thereof; and
   (b) a 1-acylceramide synthesis inhibitor or a pharmaceutically acceptable salt thereof;
   wherein said hyperproliferative disorder is a cancer selected from the group consisting of leukemia, neuroblastoma, lung cancer, skin cancer, prostate cancer, colon cancer, breast cancer, and pancreatic cancer;
   and wherein the retinoic acid derivative is given in an amount effective to produce necrosis, apoptosis, or both in the cancer, and the 1-acylceramide synthesis inhibitor is given in an amount effective to increase the necrosis, apoptosis or both produced in the cancer over that expected to be produced by the sum of that produced by the retinoic acid derivative and the 1-acylceramide synthesis inhibitor when given separately.

21. A method according to claim 20, wherein said ceramide-generating retinoid is fenretinide or a pharmaceutically acceptable salt thereof.

22. A method according to claim 20, wherein said 1-acylceramide synthesis inhibitor is a 1-acylceramide synthase inhibitor or a pharmaceutically acceptable salt thereof.

23. A method according to claim 20, wherein said glucosyl ceramide synthesis inhibitor is 1-phenyl-2-palmitoylamino-3-morpholino-1-propanol or a pharmaceutically acceptable salt thereof.

24. A method of treating a hyperproliferative disorder in a subject in need of such treatment, comprising administering to said subject, in combination, a treatment effective amount of:
   (a) a ceramide-generating retinoid comprising a retinoic acid derivative or a pharmaceutically acceptable salt thereof; and (b) at least two compounds selected from the group consisting of (i) 1-acylceramide synthesis inhibitors and the pharmaceutically acceptable salts thereof, (ii) sphingosine-1-phosphate synthesis inhibitors and the pharmaceutically acceptable salts thereof, and (iii) protein kinase C inhibitors and the pharmaceutically acceptable salts thereof;

wherein said hyperproliferative disorder is a cancer selected from the group consisting of leukemia, neuroblastoma, lung cancer, skin cancer, prostate cancer, colon cancer, breast cancer, and pancreatic cancer;

and wherein the retinoic acid derivative is given in an amount effective to produce necrosis, apoptosis, or both in the cancer, and the at least two compounds are given in an amount effective to increase the necrosis, apoptosis or both produced in the cancer over that expected to be produced by the sum of that produced in the retinoic acid derivative and the at least two compounds when given separately.

25. A method according to claim 24, wherein said ceramide generating retinoid is fenretinide or a pharmaceutically acceptable salt thereof.

26. A method according to claim 24, wherein said at least two compounds comprise (i) a 1-acylceramide synthesis inhibitor or a pharmaceutically acceptable salt thereof and (ii) either a sphingosine-1-phosphate, synthesis inhibitor, a protein kinase C inhibitor, or a pharmaceutically acceptable salt thereof.

27. A method according to claim 24, wherein said at least two compounds comprise a 1-acylceramide synthesis inhibitor or a pharmaceutically acceptable salt thereof, and a sphingosine-1-phosphate synthesis inhibitor or a pharmaceutically acceptable salt thereof.

28. A method according to claim 24, wherein said at least two compounds comprise a 1-acylceramide synthesis inhibitor or a pharmaceutically acceptable salt thereof, and a protein kinase C inhibitor or a pharmaceutically acceptable salt thereof.

29. A method according to claim 24, wherein said at least two compounds comprise a sphingosine-1-phosphate synthesis inhibitor or a pharmaceutically acceptable salt thereof, and a protein kinase C inhibitor or a pharmaceutically acceptable salt thereof.

30. A method according to claim 24, wherein said at least two compounds comprise a 1-acylceramide synthesis inhibitor or a pharmaceutically acceptable salt thereof, a sphingosine-1-phosphate synthesis inhibitor or a pharmaceutically acceptable salt thereof, and a protein kinase C inhibitor or a pharmaceutically acceptable salt thereof.

* * * * *

UNITED STATES PATENT AND TRADEMARK OFFICE
CERTIFICATE OF CORRECTION

PATENT NO. : 6,368,831 B1
DATED : April 9, 2002
INVENTOR(S) : Maurer et al.

It is certified that error appears in the above-identified patent and that said Letters Patent is hereby corrected as shown below:

Column 4,
Line 67, should read as follows:
-- cantly reduced by the pan-caspace enzyme BOC-d-fmk --

Column 23,
Line 53, should read as follows:
-- subject in need of such treatment, comprising administering to --

Signed and Sealed this

Eighth Day of October, 2002

*Attest:*

*Attesting Officer*

JAMES E. ROGAN
*Director of the United States Patent and Trademark Office*